(12) United States Patent
Kao et al.

(10) Patent No.: US 11,717,440 B2
(45) Date of Patent: Aug. 8, 2023

(54) METHOD AND DEVICE FOR TREATING EYE DISEASE

(71) Applicant: Avisi Technologies, LLC, Dover, DE (US)

(72) Inventors: Brandon Wei-Hsiang Kao, Placentia, CA (US); Adarsh Narayan Battu, Fremont, CA (US); Rui Jing Jiang, Lexington, MA (US)

(73) Assignee: Avisi Technologies, Inc., Redwood City, CA (US)

( * ) Notice: Subject to any disclaimer, the term of this patent is extended or adjusted under 35 U.S.C. 154(b) by 687 days.

(21) Appl. No.: 16/254,765

(22) Filed: Jan. 23, 2019

(65) Prior Publication Data

US 2019/0224047 A1    Jul. 25, 2019

Related U.S. Application Data

(60) Provisional application No. 62/794,139, filed on Jan. 18, 2019, provisional application No. 62/620,922, filed on Jan. 23, 2018.

(51) Int. Cl.
*A61F 9/007* (2006.01)

(52) U.S. Cl.
CPC .. *A61F 9/00781* (2013.01); *A61F 2220/0016* (2013.01); *A61F 2230/0004* (2013.01); *A61F 2230/0019* (2013.01); *A61F 2230/0021* (2013.01); *A61F 2230/0023* (2013.01)

(58) Field of Classification Search
CPC .......... A61F 9/00781; A61F 2220/0016; A61F 2230/0023; A61F 2230/0019; A61F 2230/0021; A61F 2230/0004; A61F 2011/085
See application file for complete search history.

(56) References Cited

U.S. PATENT DOCUMENTS

| | | | |
|---|---|---|---|
| 4,521,210 A * | 6/1985 | Wong | A61F 9/00781 623/905 |
| 5,411,473 A | 5/1995 | Ahmed | |
| 5,433,701 A | 7/1995 | Rubinstein | |
| 5,601,094 A * | 2/1997 | Reiss | A61F 9/00781 604/8 |
| 6,050,970 A | 4/2000 | Baerveldt | |
| 6,638,239 B1 | 10/2003 | Bergheim et al. | |
| 8,246,569 B1 | 8/2012 | Meng et al. | |

(Continued)

FOREIGN PATENT DOCUMENTS

| | | |
|---|---|---|
| JP | 2002-521145 A | 7/2002 |
| JP | 2017-506139 A | 3/2017 |

(Continued)

OTHER PUBLICATIONS

PCT Search Report and Written Opinion from corresponding PCT Application No. PCT/US2019/14663, dated Apr. 23, 2019, pp. 1-12.

(Continued)

*Primary Examiner* — Javier G Blanco
(74) *Attorney, Agent, or Firm* — K&L Gates, LLP

(57) ABSTRACT

Described herein is a device for lowering intraocular pressure, the device comprising a plate structure comprising an upper surface opposite a lower surface, the plate structure formed from a multi-directional plate having a plate thickness ranging from about 1 nm to about 1,000 nm.

8 Claims, 27 Drawing Sheets

(56) References Cited

U.S. PATENT DOCUMENTS

| | | | |
|---|---|---|---|
| 2004/0254521 A1* | 12/2004 | Simon | A61F 9/00781 604/8 |
| 2004/0260227 A1* | 12/2004 | Lisk, Jr. | A61F 9/00781 623/4.1 |
| 2005/0125003 A1 | 6/2005 | Pinchuk et al. | |
| 2005/0184004 A1* | 8/2005 | Rodgers | B01D 67/0062 623/4.1 |
| 2005/0267398 A1 | 12/2005 | Protopsaltis et al. | |
| 2005/0283108 A1 | 12/2005 | Savage | |
| 2009/0177138 A1 | 7/2009 | Brown et al. | |
| 2010/0004635 A1 | 1/2010 | Lin et al. | |
| 2010/0249691 A1* | 9/2010 | Van Der Mooren | A61F 9/00781 604/9 |
| 2013/0150773 A1 | 6/2013 | Nissan et al. | |
| 2015/0018746 A1 | 1/2015 | Hattenbach | |
| 2015/0230983 A1 | 8/2015 | Johnson | |
| 2017/0020730 A1* | 1/2017 | Chew | B29C 45/1671 |
| 2017/0183772 A1 | 6/2017 | Bargatin et al. | |
| 2020/0173019 A1 | 6/2020 | Bargatin et al. | |

FOREIGN PATENT DOCUMENTS

| | | |
|---|---|---|
| JP | 2017-519592 A | 2/2021 |
| WO | 2010111528 | 9/2010 |
| WO | 2016/044173 A1 | 3/2016 |
| WO | 2016044173 | 3/2016 |
| WO | 2016/140334 A1 | 2/2018 |
| WO | 2018156687 | 8/2018 |

OTHER PUBLICATIONS

European Communication Supplementary European Search Report, Appl. No. 19743528.2 PCT/US2019014663 dated Sep. 16, 2021—7 pages.

Office Action for Japanese Application No. 2020-561580, dated Feb. 21, 2023, in 11 pages.

* cited by examiner

METHOD AND DEVICE FOR TREATING EYE DISEASE

CROSS-REFERENCE TO RELATED APPLICATIONS

This application claims the benefit of U.S. Provisional Application No. 62/620,922, filed Jan. 23, 2018 and U.S. Provisional Application No. 62/794,139, filed on Jan. 18, 2019. The disclosures of the above applications are incorporated herein by reference.

BACKGROUND

Millions of individuals suffer from eye disease, specifically glaucoma. Most glaucoma patients are associated with abnormally high intraocular pressure (IOP) due to the patient's inability to drain excessive aqueous humor from the anterior chamber of the eye through the trabecular meshwork. If not reduced with adequate treatment, the high LOP would continuously damage the optic nerve as the disease progresses, leading to loss of vision or even total blindness. Current medications, surgeries, and implants have proven inadequate in lowering pressure within the eye or sustaining normal eye pressure over many years. Therefore, the need exists for new ways to alleviate LOP, thereby treating glaucoma.

BRIEF SUMMARY

Described herein is a device for lowering intraocular pressure, the device comprising: a plate structure comprising a first major exposed surface opposite a second major exposed surface, the plate structure formed from a multi-directional plate having a plate thickness ranging from about 1 nm to about 1,000 nm.

In other embodiments, the present invention includes a method of reducing intraocular pressure comprising: a) securing a treatment device to an eye, the treatment device comprising a plate structure having an upper surface opposite a lower surface, the plate structure formed from a multi-directional plate having a thickness ranging from about 1 nm to about 1,000 nm.

Other embodiments of the present invention include a device for lowering intraocular pressure, the device comprising: a plate structure comprising an upper surface opposite a lower surface, the lower surface comprising a plurality of open channels; wherein the plate structure has a height ranging from about 5 μm to about 20 μm as measured by the distance between the upper surface and the lower surface of the plate structure.

Other embodiments of the present invention include a device for lowering intraocular pressure, the device comprising: a first plate structure comprising an upper surface opposite a lower surface, the first plate structure formed from a first multi-directional plate having a plate thickness ranging from about 1 nm to about 1,000 nm; a second plate structure comprising an upper surface opposite a lower surface, the second plate structure formed from a second multi-directional plate having a plate thickness ranging from about 1 nm to about 1,000 nm.

Other embodiments of the present invention include a device for lowering intraocular pressure, the device comprising: a plate structure having a first major surface opposite a second major surface, the plate structure comprising a multi-directional plate having a thickness ranging from about 1 nm to about 1,000 nm; and a penetrating element secured to the first major surface of the plate structure.

Other embodiments of the present invention include a method of reducing intraocular pressure comprising: implanting a treatment device in anterior portion of an eye, the treatment device comprising a plate structure formed from a multi-directional plate, whereby after implantation the a first end of the plate structure is located between sclera and conjunctiva of the eye.

Other embodiments of the present invention include a method of reducing intraocular pressure comprising: a) securing a treatment device to an eye, the treatment device comprising a plate structure comprising an uppermost surface opposite a lowermost surface; a plurality of open channels formed into the lower most surface; wherein the plate structure has a height ranging from about 5 μm to about 20 μm as measured by the distance between the uppermost surface and the lowermost surface of the plate structure.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 7 is a cross-sectional view the eye of FIG. 5 comprising the treatment device implanted there-on;

DETAILED DESCRIPTION

Figure 1:
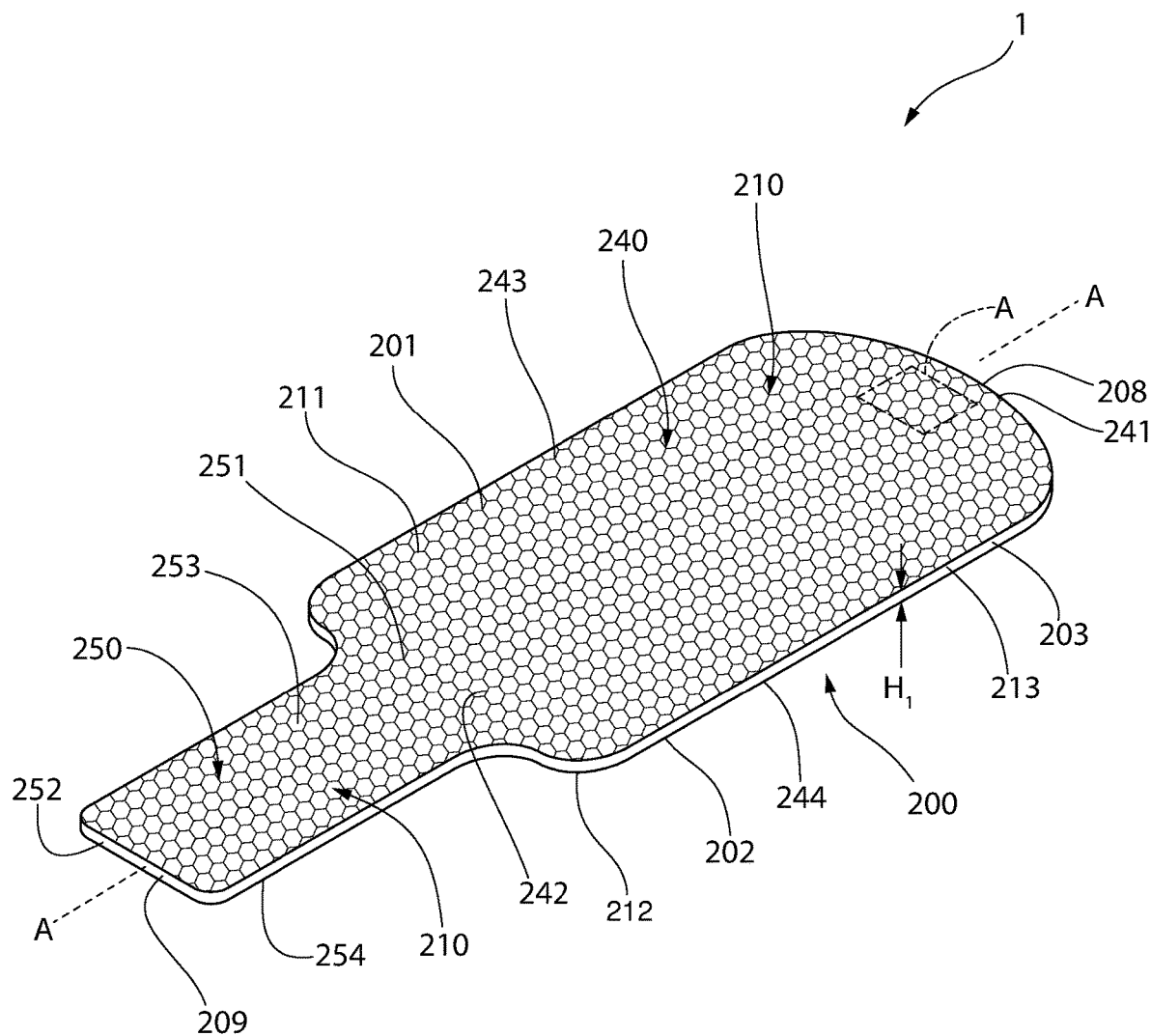
FIG. 1 is a perspective view of a treatment device according to the present invention.

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top," and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the structure be constructed or operated in a particular orientation unless explicitly indicated as such.

Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Unless otherwise specified, all percentages and amounts expressed herein and elsewhere in the specification should be understood to refer to percentages by weight. The amounts given are based on the weight of the material. According to the present application, the term "about" means +/−5% of the reference value. According to the present application, the term "substantially free" means less than about 0.1 wt. % based on the total of the referenced value.

A "subject" herein may be a human or a non-human animal, for example, but not by limitation, rodents such as mice, rats, hamsters, and guinea pigs; rabbits; dogs; cats; sheep; pigs; goats; cattle; horses; and non-human primates such as apes and monkeys, etc.

Referring to FIGS. 1-4, the present invention includes a treatment device 1 (also referred to as a "device") for lowering intraocular pressure. Additionally, the device 1 of the present invention may provide improvements in treating eye disease—specifically glaucoma.

The device 1 may comprise a plate structure 200 having a first major exposed surface 201 opposite a second major exposed surface 202 as well as a side surface 203 extending there-between. The plate structure 200 may comprise an uppermost surface 206 that is opposite a lowermost surface 207. The first major exposed surface 201 may comprise the uppermost surface 206 of the plate structure 200. The second major exposed surface 202 may comprise the lowermost surface 207 of the plate structure 200.

The overall shape of first major exposed surface 201 and second major exposed surface 202 of the plate structure 200 may be defined by the side surface 203. The side surface 203 may define a perimeter of the first and second major exposed surfaces 201, 202. The overall shape of the plate structure may be selected from a variety of geometries. Non-limiting examples of such geometries include polygonal shape, circular shape, mushroom shape, elliptic shape, oblong shape, oval shape, amoeba shape, or butterfly shape with lateral wings.

The plate structure 200 may have a plate structure height $H_1$, which is the overall distance measured between the uppermost surface 206 and the lowermost surface 207 of the plate structure 200. The plate structure height $H_1$ may range from about 5 µm to about 20 µm—including all distances and sub-ranges there-between.

The plate structure 200 may be at least partially formed from a multi-directional plate 210 (also referred to as the "plate" 210). The plate 210 is a three-dimensional body. The plate 210 may comprise a first major surface 211 that is opposite a second major surface 212 and a side surface 213 that extends between the first and second major surfaces 211, 212. When viewed with the naked eye, the first major surface 211 of the plate 210 may be substantially continuous and appear smooth. When viewed with the naked eye, the second major surface 212 of the plate 210 may be substantially continuous and appear smooth. The plate 210 may be translucent. The plate 210 may be light-transmissive.

The plate 210 may have a thickness T as measured by the distance extending between the adjacent-most portions of the first major surface 211 and the second major surface 212 of the plate 210 in an orthogonal direction to the first and second major surfaces 211, 212. The thickness T may range from about 1 nm to about 1,000 nm—including all thicknesses and sub-ranges there-between. In some embodiments, the thickness T may range from about 50 nm to about 500 nm—including all thicknesses and sub-ranges there-between. In some embodiments, the thickness T may range from about 100 nm to about 400 nm—including all thicknesses and sub-ranges there-between. In some embodiments, the thickness T may range from about 100 nm to about 250 nm—including all thicknesses and sub-ranges there-between. In some embodiments, the thickness T may range from about 250 nm to about 500 nm—including all thicknesses and sub-ranges there-between. In some embodiments, the thickness T may range from about 300 nm to about 550 nm—including all thicknesses and sub-ranges there-between.

The multi-directional plate 210 may be a single layer that is patterned in three-dimensional space, thereby forming the multi-directional geometry of the multi-directional plate 210. While the geometry of the multi-directional plate 210 may result in the overall plate structure 200 having a height H as greater as 20 μm, the thickness of the multi-directional plate 210—i.e., the thickness of the single layer that is patterned into the multi-directional plate 210—remains within the aforementioned thickness T range of 1 nm to 1,000 nm.

In some embodiments, the first major surface 211 of the plate 210 may at least partially make up the first exposed major surface 201 of the plate structure 200. Stated otherwise, the first exposed major surface 201 of the plate structure 200 may at least partially comprise the first major surface 211 of the plate 210. In some embodiments, the second major surface 212 of the plate 210 may at least partially make up the second exposed major surface 202 of the plate structure 200. Stated otherwise, the second exposed major surface 202 of the plate structure 200 may at least partially comprise the second major surface 212 of the plate 210. In some embodiments, the side surface 213 of the plate 210 may at least partially make up the side surface 203 of the plate structure 200. Stated otherwise, the side surface 203 of the plate structure 200 may at least partially comprise the side surface 213 of the plate 210.

Figure 4:
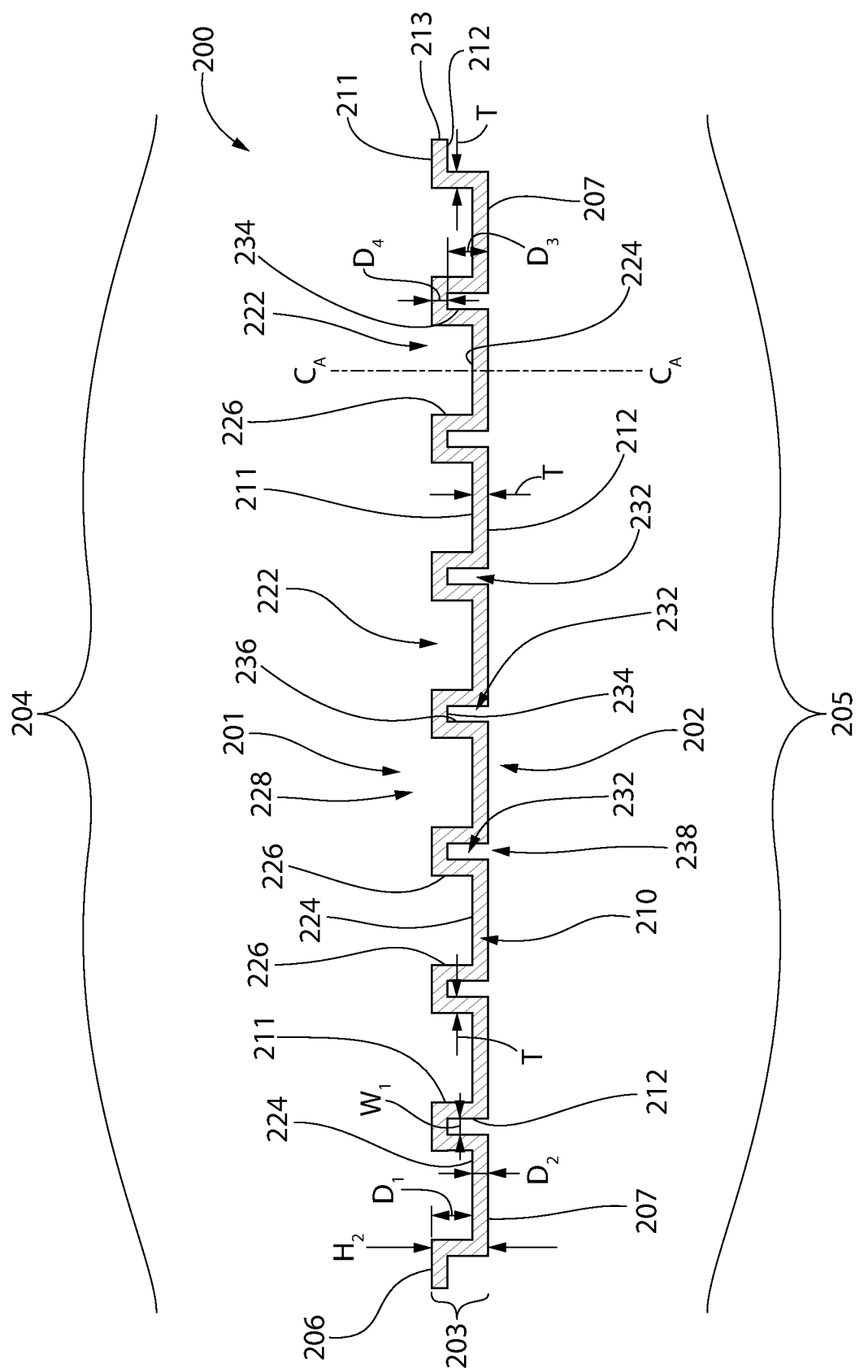
FIG. 4 is a cross-sectional view of the treatment device shown along line IV-IV in FIG. 3.

Referring now to FIG. 4 in particular, the first major exposed surface 201 of the plate structure 200 may comprise a first topography 204. The first topography 204 may be created by the first major surface 211 of the plate 210 as a result of the multi-directional patterned geometry of the multi-directional plate 210. The first topography 204 may comprise surface features that are formed into the uppermost surface 206 of the plate structure 200, whereby the surface features extend from the uppermost surface 206 in a direction toward the lowermost surface 207 of the plate structure 200 and terminate at a floor 224—as discussed in greater detail herein.

The plate structure 200 may further comprise a second topography 205. The second topography 205 may be created by the second major surface 212 of the plate 210 as a result of the multi-directional patterned geometry of the multi-directional plate 210. The second topography 205 may comprise surface features that are formed into the lowermost surface 207 of the plate structure 200, whereby the surface features extend from the lowermost surface 207 in a direction toward the uppermost surface 206 of the plate structure 200 and terminate at a ceiling 234—as discussed in greater detail herein.

The surface features of the first topography 204 and/or second topography 205 may comprise one or more cells 222. As described in greater detail herein, the cells 222 may be open cells. In other embodiments, the surface features of the first topography 204 and/or second topography 205 may comprise one or more channels 232. As described in greater detail herein, the channels 232 may be open channels.

Although not limited to, the foregoing discussion will reference the first topography 204 comprising one or more cells 222 and the second topography 205 comprising one or more channels 232. Although not pictured, other embodiments of the present invention include that the first topography 204 may comprise one or more channels 232 and the second topography 205 may comprise one or more cells 222.

Each cell 222 may comprise a cell floor 224 and at least one cell wall 226. The cell wall 226 may circumscribe the cell floor 224. The cell walls 226 may extend downward from the uppermost surface 206 of the plate structure 200 to the cell floor 224 in a direction toward the lowermost surface 207 of the plate structure 200, whereby the cell walls 226 may terminate at the cell floor 224. The cell walls 226 may extend upward from the cell floor 224 in a direction toward the uppermost surface 206 of the plate structure 200, whereby the cell walls 226 may terminate at the uppermost surface 206 of the plate structure 200.

Each of the cells 222 may comprise a cell axis $C_A$-$C_A$. The cell axis $C_A$-$C_A$ is oriented substantially normal to the floor surface 224. The cell wall surface 226 may be oriented about the cell axis $C_A$-$C_A$.

The cell walls 226 may form a perimeter of each cell 222. Although not pictured, the cell walls 226 may be a single continuous wall surface, whereby the cell 222 forms a cylindrical shape. Non-limiting examples of cylindrical shapes include circular cylinders as well as elliptical cylinders. As demonstrated by FIG. 3, other embodiments provide that each cell 222 may be formed from a plurality of cell walls 226 that intersect each other to form a polygonal perimeter. In such embodiments, although not limited to, the number of cell walls 226 that form a polygonal perimeter may range from 3 to 20 sides—including all sides and sub-ranges there-between. In the embodiment exemplified in FIG. 3, each cell 222 is formed from six intersecting cell walls 226 that form a hexagonal perimeter.

Collectively, the uppermost surface 206, the cell wall 226, and the cell floor 224 may form at least a portion of the first major exposed surface 201 of the plate structure 200. The first major surface 211 of the plate 210 may comprise the first major exposed surface 201 of the plate structure 200. Stated otherwise, the first major surface 211 of the plate 210 may comprise the uppermost surface 206 as well as the cell wall 226 and the cell floor 224 formed by the first topography 204.

Each cell 222 may further comprise an open-end 228 that is located opposite the cell floor 224. The cell axis $C_A$-$C_A$ may intersect the open-end 228. The open-end 228 may be a fluid pathway that provides access the open volume of the cell 222 located between the cell wall surface 226 and the floor surface 224. Stated otherwise, each of the cells 222 may be open (also referred to as "open-ended") such that no ceiling exists opposite the cell floor 224, which would otherwise close the cell 222 and encapsulate the open volume of the cell 222.

Each of the cells 222 may be isolated from each other by their respective cell walls 226, such that the open volume of each cell 222 is not in fluid communication with other open-volumes of other cells 222.

The first topography 204 may be formed by the multi-directional nature of the multi-directional plate 210. As a result, the dimensions of the plate structure 200—specifically the dimensions of the first topography 204, may be determined with respect to the thickness T of the plate 210.

For each cell 222, the cell floor 224 may be offset from the uppermost surface 206 of the plate structure 200 by a first distance $D_1$ (also referred to herein as "cell depth"). Although not limited to, the offset between the uppermost surface 206 and the floor surface 224 may be referred to as a "vertical offset" or "vertically offset." The first distance $D_1$ is a non-zero value. The first distance $D_1$ may be equal to the difference between the first height $H_2$ of the plate structure 200 and the thickness T of the plate 210—whereby the first distance $D_1$ is calculated according to the following formula:

$$D_1 = H_2 - T$$

For each cell 222, the cell floor 224 may be offset from the lowermost surface 207 by a second distance $D_2$. Although not limited to, the offset between the lowermost surface 207 and the floor surface 224 may be referred to as a "vertical offset" or "vertically offset." The second distance $D_2$ is a non-zero value. The second distance $D_2$ may be substantially equal to the thickness T of the plate 210. The summation of the first distance $D_1$ and the second distance $D_2$ may be substantially equal to the first height $H_2$.

Figure 3:
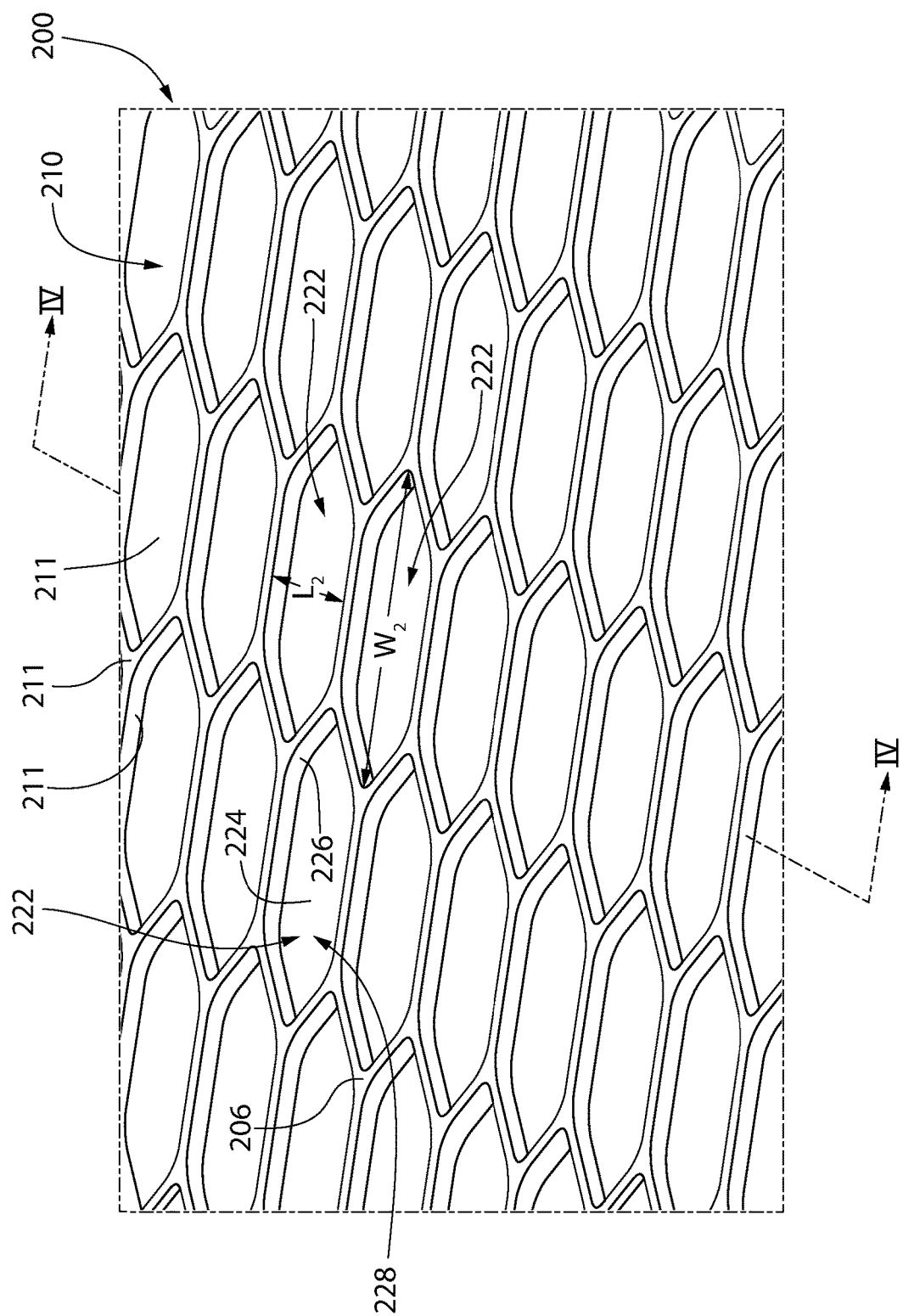
FIG. 3 is a close-up view of the treatment device according to section A identified in FIG. 1.

Referring now to FIGS. 3 and 4, each cell 222 may have a cell length $L_2$ and a cell width $W_2$ as measured by the distance extending between opposite cell walls 226 within each cell 222. In some embodiments, the cell length $L_2$ and the cell width $W_2$ may be equal. In other embodiments, the cell length $L_2$ and the cell width $W_2$ may be different. The cell length $L_2$ may range from about 10 μm to about 110 μm—including all lengths and sub-ranges there-between. In some embodiments, the cell length $L_2$ may range from about 30 μm to about 70 μm—preferably from about 40 μm to about 60 μm—including all lengths and sub-ranges there-between. The cell width $W_2$ may range from about 10 μm to about 110 μm—including all lengths and sub-ranges there-between. In some embodiments, the cell width $W_2$ may range from about 30 μm to about 70 μm—preferably from about 40 μm to about 60 μm—including all lengths and sub-ranges there-between.

Each channel 232 may be formed by a channel ceiling 234 and at least one channel wall 236. The channel walls 236 may extend downward from the channel ceiling 234 and in a direction toward the lowermost surface 207 of the plate structure 200, whereby the channel walls 236 terminate at the lowermost surface 207 of the plate structure 200. The channel walls 236 may extend upward from the lowermost surface 207 in a direction toward the channel ceiling 234, whereby the channel walls 236 may terminate at the channel ceiling 234.

Collectively, the lowermost surface 207, the channel wall 236, and the channel ceiling 234 may form at least a portion of the second major exposed surface 202 of the plate structure 200. The second major surface 212 of the plate 210 may comprise the second major exposed surface 202 of the plate structure 200. Stated otherwise, the second major surface 212 of the plate 210 may comprise the lower surface 207 as well as the channel wall 236 and the channel floor 234 formed by the second topography 205.

Each channel 232 may further comprise an open-end 238 that is located opposite the channel ceiling 234. The open-end 238 may be a fluid pathway that provides access the open volume of the channel 232 located between the channel walls 236 and the channel ceiling 234. Stated otherwise, each of the channels 232 may be open (also referred to as "open-ended") such that no floor exists opposite the channel ceiling 234, thereby closing the channel 232 or encapsulating the channel-volume that is created by the channel walls 236 and channel floors 234.

A plurality of intersecting channels 234 may be present on the second major surface 202 of the plate structure 200, thereby forming a network of channels. Each of the channels in the network may be in fluid communication with each other, thereby allowing a fluid to flow along the second major surface 202 of the plate structure 200 via the channels 232.

The second topography 205 of the present invention may be formed by the multi-directional nature of the multi-directional plate 210. As a result, the dimensions of the plate structure 200—specifically the dimensions of the second topography 205, may be determined with respect to the thickness T of the plate 210.

For each channel 232, the channel ceiling 234 may be offset from the lowermost surface 207 of the plate structure 200 by a third distance $D_3$ (also referred to herein as "channel depth"). Although not limited to, the offset between the lowermost surface 207 and the channel ceiling 234 may be referred to as a "vertical offset" or "vertically offset." The third distance $D_3$ is a non-zero value. The third distance $D_3$ may be equal to the difference between the first height $H_2$ of the plate structure 200 and the thickness T of the plate 210—whereby the third distance $D_3$ is calculated according to the following formula:

$$D_3 = H_2 - T$$

For each channel 232, the channel ceiling 234 may be offset from the uppermost surface 206 by a fourth distance $D_4$. Although not limited to, the offset between the uppermost surface 206 and the channel ceiling 234 may be referred to as a "vertical offset" or "vertically offset." The fourth distance $D_4$ is a non-zero value. The fourth distance $D_4$ may be substantially equal to the thickness T of the plate 210. The summation of the third distance $D_3$ and the fourth distance $D_4$ may be substantially equal to the first height $H_2$.

Each channel 232 may have a channel length and a channel width $W_1$. The channel width $W_1$ is measured by the distance extending between opposite channel walls 236 within each channel 222. The channel length is measured by the distance extending along the channel 232 between intersecting other channels 232. In some embodiments, the channel length is greater than the channel width $W_1$. The channel length may range from about 10 μm to about 110 μm—including all lengths and sub-ranges there-between. In some embodiments, the channel length may range from about 30 μm to about 70 μm—preferably from about 40 μm to about 60 μm—including all lengths and sub-ranges there-between. The channel width $W_1$ may range from about 10 μm to about 40 μm—including all lengths and sub-ranges there-between. In a preferred embodiment, the channel width $W_1$ may range from about 10 μm to about 15 μm—including all lengths and sub-ranges there-between.

It has been discovered that a channel depth and channel width $W_1$ of about 10 μm to 15 μm provides for normal physiologic flow of aqueous humor along the plate structure 200. The flow rate of the aqueous humor along such plate may range from about 1.75 μL/min to about 2.75 μL/min—preferably about 2 μL/min to about 2.5 μL/min—including all rates and sub-ranges there-between.

In some embodiments, the plate 210—and resulting plate structure 200—may be formed from a variety of materials. The materials forming the plate are preferably biocompatible materials. As used herein, the term "biocompatibility" refers to compatibility with living tissue or a living system by not being toxic, injurious, or physiologically reactive and not causing immunological rejection. Non-limiting examples of materials that form the plate 210 include ceramic materials, polymeric materials, metallic materials, and composite materials thereof.

Non-limiting examples of ceramic materials include alumina ($Al_2O_3$), silicon nitride ($Si_xN_y$), silica ($SiO_2$), hafnium oxide ($HfO_2$), titanium nitride ($TiN_x$), titanium carbide (TiC), derivative thereof, and a combination thereof. In a preferred embodiment, the ceramic material includes alumina. In another preferred embodiment, the ceramic material includes silicon nitride. Non-limiting examples of metallic material include platinum, gold, or tungsten.

The plate 210—and resulting plate structure 200—may have a higher flexural stiffness as compared to planar films. For example, plate 210 may have the same thickness as planar structures and have a much higher spring constant when used as cantilevers and/or doubly clamped beams. Similarly, plate 210 may have the same spring constant as planar structures and can be significantly thinner. For example, plate 210 of the present invention may be at least about 20 times thinner, at least about 15 times thinner, at least about 10 times thinner, or at least about 5 times thinner than planar structures having the same flexural stiffness.

The plate 210 of the present invention may be flexible. According to the present invention, the term "flexible" refers to the plate 210 being capable of being deformed without any or a substantial amount of fracture or permanent deformation—also referred to as having shape-recovery. Specifically, the flexibility of the plate 210 may provide that the first and second major surfaces 211, 212 can be folded at least 90° without fracture to the plate 210. In some embodiments, the plate 210 flexibility may provide that the first and second major surfaces 211, 212 can be folded up to 180° without fracture to the plate 210. Similarly, the flexibility of the plate structure 200 may provide that the first and second exposed major surfaces 201, 202 can be folded at least 90° without fracture to the plate structure 200. In some embodiments, the flexibility of the plate structure 200 may provide that the first and second exposed major surfaces 201, 202 can be folded up to 180° without fracture to the plate structure 200.

Therefore, the present invention provides for a plate 210—and resulting plate structure 200—that may be formed entirely from a metal and/or ceramic material that may also be flexible (i.e., capable of being folded up to 180°, preferably at least 90°, without fracture).

In some embodiments, plate structure 200 may be ultralight. The term "ultralight" refers to the plate structure 200—and corresponding plate 210—having a relative density on the order of about $10^{-4}$. The plate structure 200 may also have an areal density on the order of 100 milligrams per square meter. For example, the plate structure 200 may have an areal density between about 10 mg/m$^2$ and about 1000 mg/m$^2$—including all densities and sub-ranges there-between.

Figure 2:
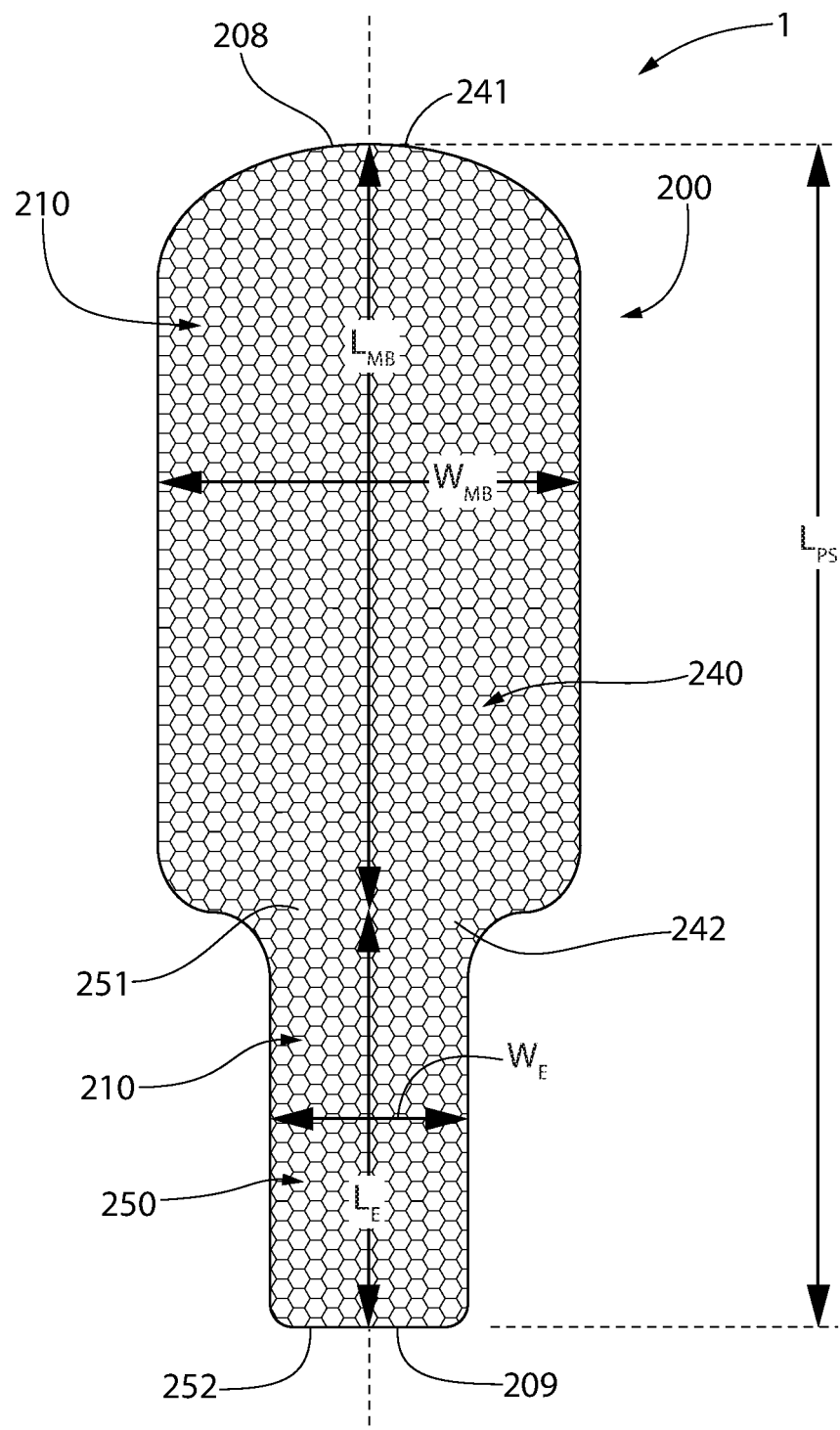
FIG. 2 is a top view of the treatment device of FIG. 1.

Referring now to FIGS. 1 and 2, the device 1 may comprise a plate structure 200 that extends along a longitudinal axis A-A. The plate structure 200 may further comprise a proximal end 208 opposite a distal end 209, whereby the longitudinal axis A-A intersects both the proximal end 208 and distal end 209 of the plate structure 200. The plate structure 200 may have an plate structure length $L_{PS}$ that spans the distance from the proximal end 208 to the distal end 209 of the plate structure 200. The plate structure length $L_{PS}$ may range from about 10 mm to about 24 mm—including all lengths and sub-ranges there-between. In a preferred embodiment, the plate structure length $L_{PS}$ may be about 17 mm.

The plate structure 200 may further comprise a main body portion 240 and an extension portion 250. The main body portion 240 may comprise a proximal end 241 that is opposite a distal end 242. The extension portion 250 may comprise a proximal end 251 that is opposite a distal end 252. The proximal end 251 of the extension portion 250 may extend from the distal end 242 of the main body portion 240. The proximal end 241 of the main body portion 240 may overlap with the proximal end 208 of the plate structure 200. The distal end 252 of the extension portion 250 may overlap with the distal end 209 of the plate structure 200.

The main body portion 240 may comprise a first major surface 243 that is opposite a second major surface 244. The first major exposed surface 201 of the plate structure 200 may comprise the first major surface 243 of the main body portion 240. The second major exposed surface 202 of the plate structure 200 may comprise the second major surface 244 of the main body portion 240.

The main body portion 240 may extend a main body length $L_{MB}$ that spans the distance from the proximal end 241 to the distal end 242 of the main body portion 240. The main body length $L_{MB}$ may range from about 8 mm to about 16 mm—including all lengths and sub-ranges there-between. In a preferred embodiment, the main body length $L_{MB}$ may be about 12 mm.

The main body portion 240 may have a main body width $W_{MB}$ that as measured by the distance spanning the direction extending normal to the longitudinal axis A-A. The main body width $W_{MB}$ may range from about 4 mm to about 8 mm—including all lengths and sub-ranges there-between. In a preferred embodiment, the main body width $W_{MB}$ may be about 6 mm.

The extension portion 250 may comprise a first major surface 253 that is opposite a second major surface 254. The first major exposed surface 201 of the plate structure 200 may comprise the first major surface 253 of the extension portion 250. The second major exposed surface 202 of the plate structure 200 may comprise the second major surface 254 of the extension portion 250.

The extension portion 250 may extend an extension length $L_E$ that spans the distance from the proximal end 251 to the distal end 252 of the extension portion 250. The extension length $L_E$ may range from about 1 mm to about 4 mm—including all lengths and sub-ranges there-between. In a preferred embodiment, the extension length $L_E$ may be about 2 mm.

The extension portion 250 may have an extension width $W_E$ that as measured by the distance spanning the direction extending normal to the longitudinal axis A-A. The extension width $W_E$ may range from about 1.0 mm to about 6.0 mm—including all lengths and sub-ranges there-between. In a preferred embodiment, the extension width $W_E$ may be about 2.6 mm.

In some embodiments, the main body length $L_{MB}$ and the extension length $L_E$ may be equal. In other embodiments, the main body length $L_{MB}$ and the extension length $L_E$ may be different. In some embodiments, a ratio of the main body length $L_{MB}$ to the extension length $L_E$ may range from about 1:1 to about 5:1—including all ratios and sub-ranges there-between. In some embodiments, the ratio of the main body length $L_{MB}$ to the extension length $L_E$ is greater than 1:1. In some embodiments, the ratio of the main body length $L_{MB}$ to the extension length $L_E$ may range from about 3:1 to about 5:1—including all ratios and sub-ranges there-between.

In some embodiments, the main body width $W_{MB}$ and the extension width $W_E$ may be equal. In other embodiments, the main body width $W_{MB}$ and the extension width $W_E$ may be different. In other embodiments, the main body width $W_{MB}$ may be greater than the extension width $W_E$. In some embodiments, a ratio of the main body width $W_{MB}$ to the extension width $W_E$ may range from about 1:1 to about 4:1—including all ratios and sub-ranges there-between. In some embodiments, a ratio of the main body width $W_{MB}$ to the extension width $W_E$ may range from about 1.1:1 to about 4:1—including all ratios and sub-ranges there-between. In some embodiments, the ratio of the main body width $W_{MB}$ to the extension width $W_E$ may range from about 1.5:1 to about 3:1—including all ratios and sub-ranges there-be-tween.

The first major surface 253 of the extension portion 250 may be substantially coplanar with the first major surface 243 of the main body portion 240. The second major surface 254 of the extension portion 250 may be substantially coplanar with the second major surface 244 of the main body portion 240.

The main body portion 240 may have a height, as measured by the distance between the first and second major surfaces 243, 244 of the main body portion 240, that is substantially equal to the first height $H_1$ of the plate structure 200. The extension portion 250 may have a height, as measured by the distance between the first and second major surfaces 243, 244 of the extension portion 250, that is substantially equal to the first height $H_1$ of the plate structure 200.

Referring now to FIGS. 5-8, the treatment device 1 of the present invention may be positioned in contact with an eye 900 for the treatment of an eye disease. Non-limiting examples of such eye disease include glaucoma. The eye 900 generally comprises outer tissue comprising the sclera 913, cornea 910, conjunctiva 950, and limbus. Within the eye 900, two chambers exist that include the posterior cavity 995 which is located behind leans 930 of the eye 900, and the anterior chamber 990 which is located in front of the lends 930 of the eye 900. The posterior cavity 995 houses vitreous humor and the anterior chamber 990 houses aqueous humor.

As described herein, the eye 900 comprises a front region 901 and a rear region 902, whereby a boundary 903 generally exists between the front region 901 and the rear region 902. The front region 901 of the eye 900 comprises the cornea 910, iris 911, pupil 912, conjunctiva tissue 950, ciliary body 915 and the lens 930, a portion of the sclera 913, as well as encompasses the anterior chamber 990 of the eye 900. The front region 901 may further comprise a limbal region 980, a corneo-limbal region 982, and anterior scleral region 950.

The rear region 902 comprises eye muscle tissue 920 (also referred to as "eye muscles"), a portion of the sclera 913, the optic nerve 942, the retina 941, as well as encompasses the posterior cavity 995 of the eye 900. The eye muscles 920 are present in the orbital cavity of a subject. The eye muscles 920 comprise the superior rectus muscle 921 located at a top portion of the eye 900, the inferior rectus muscle 922 located at a bottom portion of the eye 900, and the lateral rectus muscle 923 located between the superior rectus muscle 921 and the inferior rectus muscle 922.

The present invention includes a method for treating eye disease—such as glaucoma—by lowering intraocular pressure of a subject using the treatment device 1. Specifically, the treatment device 1 provides a fluid pathway for excess fluid present in either the anterior chamber 990 and/or the posterior cavity 995 to exit the eye 900. In a preferred embodiment, the treatment device 1 lowers intraocular pressure of the subject by providing a fluid pathway for excess fluid to exit the anterior chamber 990 to a location exterior the sclera 913.

The term "excess fluid" refers to an additional volume of aqueous humor present in the anterior chamber 990 that raises the intraocular pressure to be greater than a normal intraocular pressure for a healthy eye. For eyes 900 that cannot release such excess fluid, the increased intraocular pressure is a factor contributing to blindness in glaucoma patients. Therefore, providing a fluid pathway for the excess fluid to be expelled from the anterior chamber 990 of the eye 900 can help reduce intraocular pressure, thereby helping treat glaucoma.

In non-limiting embodiments, the methods described herein may be suitable for treating any types of ophthalmic condition related to intraocular pressure. Non-limiting examples of ophthalmic condition include primary open-angle glaucoma, normal-tension glaucoma, ocular hypertension, primary angle closure glaucoma, congenital and juvenile glaucoma, and secondary glaucomas, including exfoliative, uveitic, neovascular, pigmentary and other secondary glaucomas. In particular, the ophthalmic condition include glaucoma and all subtypes of glaucoma.

The treatment device 1 of the present invention provides such fluid pathway for excess fluid to exit the eye 900. Specifically, the treatment device 1 may be implanted onto the eye 900 such that it creates a fluid pathway from the anterior chamber 990 to the exterior of the sclera 913 to form a subconjunctival bleb. The term "subconjunctival bleb" refers to a fluid pocket containing aqueous humor, wherein the fluid pocket is located between conjunctiva and sclera tissues. Once on the exterior surface of the sclera 913, the excess fluid can be carried away from the eye 900 by absorption into surrounding tissue in the subject.

In particular, the treatment device 1 may be implanted onto the eye 900 such that the plate structure 200 is located between the sclera 913 and conjunctiva 950 tissue. The extension portion 250 may extend from the main body portion 240 through the sclera 913 and into the anterior chamber 990 of the eye 900 such that the distal end 209 of the plate structure 200 is located within the anterior chamber 990. Under this configuration, the plate structure 200 may function as an external reservoir for the excess fluid until it is absorbed by the surrounding tissue of the subject. In certain embodiments, prior to implanting the treatment device 1, the plate structure 200 may be sterilized to minimize postoperative complications.

The extension portion 250 may extend from the main body portion 240 through the sclera 913 and into the anterior chamber 990 of the eye 900 (as shown in the FIGS) or may extend from the main body portion 240 through the sclera 913 and into the posterior cavity 989 of the anterior chamber 990 of the eye 900. The treatment device 1 may be implanted such that the extension portion 250 extends through the limbal region 980, the corneal limbal region 981, or the anterior scleral region 982.

In such embodiments, the first and/or second topographies 204, 205 of the plate structure 200 may provide the fluid pathway for the excess fluid to exit the anterior chamber 990 of the eye 900, thereby relieving excess intraocular pressure.

The treatment device 1 may be implanted such that the treatment device 1 is secured to the eye 900. In some embodiments, the treatment device 1 may be implanted between the conjunctiva 950 and the sclera 913. In a non-limiting example, a conjunctival incision can be created to allow adequate exposure for insertion of the treatment device 1. In a non-limiting embodiment, the treatment device 1 may be secured any eye 900 by suture or extending through the plate structure 200 to the sclera 913.

Once implanted, the first major exposed surface 201 of the plate structure 200 may face the sclera 913 and the second major exposed surface 202 of the plate structure 200 may face the conjunctiva 950. In such embodiments, the first major exposed surface 201 of the plate structure 200 may contact the sclera 913 and the second major exposed surface 202 of the plate structure 200 may contact the conjunctiva 950. In other embodiments, the treatment device 1 may be implanted such that the first major exposed surface 201 of the plate structure 200 faces the conjunctiva 950 and the second major exposed surface 202 of the plate structure 200 faces the sclera 913. In such embodiments, the first major exposed surface 201 of the plate structure 200 may contact the conjunctiva 950 and the second major exposed surface 202 of the plate structure 200 may contact the sclera 913.

In other embodiments, the treatment device 1 may comprise plate structure 200 that extends from the exterior surface of the sclera 913, through the sclera 913, and into the anterior chamber 990 of the eye 900—whereby the plate structure 200 itself provides a fluid pathway for excess fluid to exit from within the eye 900. In such embodiments, the excess intraocular fluid may travel along via the treatment device 1 and exit the eye 900 by capillary action.

According to the present invention, the plate structure 200 having the previously discussed thickness T and material properties allows for placement of the treatment device 1 at least partially within the front region 901 of the eye 900. In some embodiments, the treatment device 1 may be implanted entirely within the front region 901 of the eye 900—herein referred to as "forward placement." Such forward placement may allow at least a portion of the treatment device 1 to be present on the anterior portion 901 of the eye 900—as discussed further herein. Additionally, such forward-placement of the treatment device 1 may allow a less invasive implant procedure—as compared to previous implant devices. Additionally, such forward placement may also provide greater comfort to the subject. Furthermore, the translucent appearance of the plate structure 200 may provide that the treatment device 1 is at least partially implanted within the front region 901 of the eye without the treatment device from being readily perceivable when a subject's eye 900 with viewing a naked eye.

Figure 5:
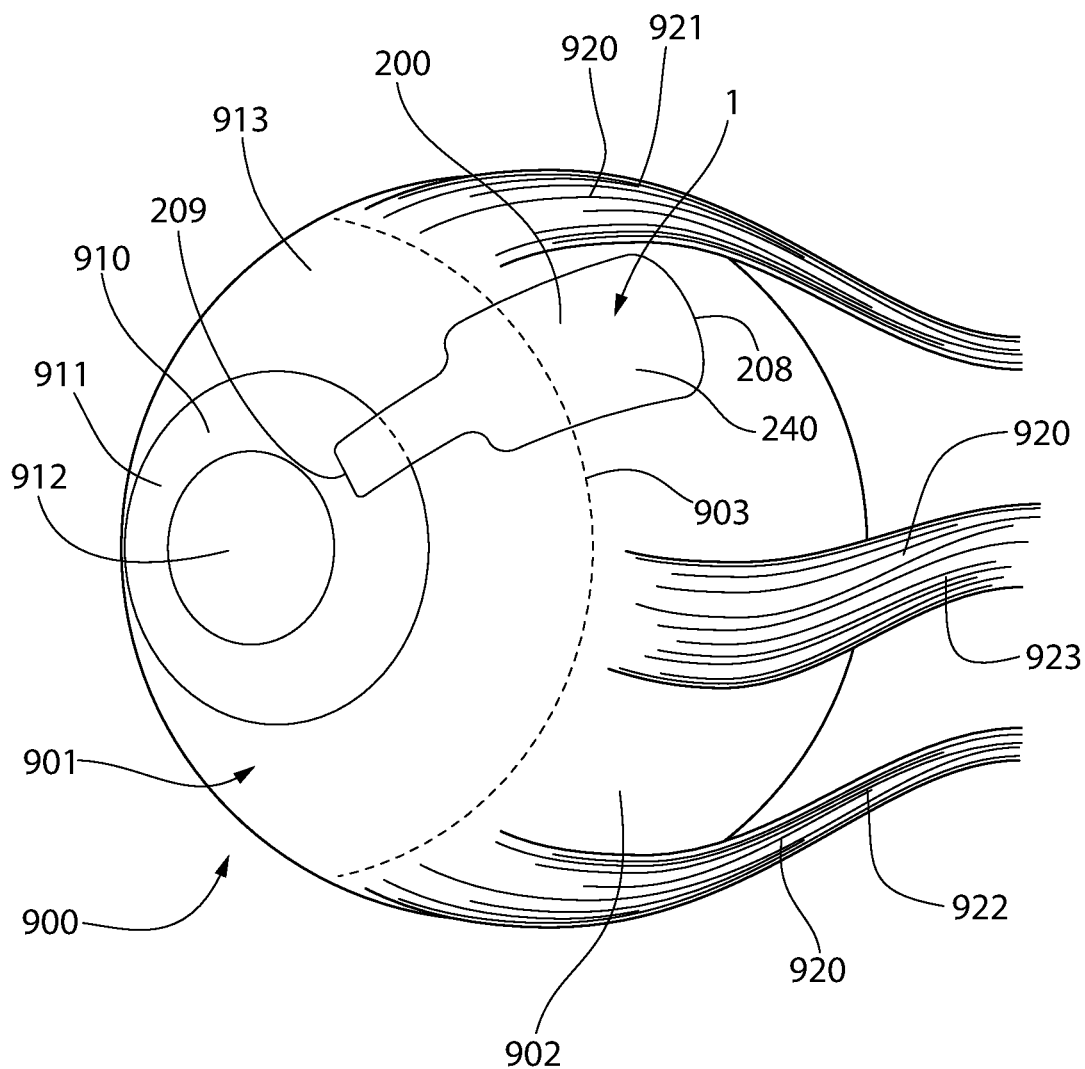
FIG. 5 is a perspective anterior view of an eye comprising the treatment device of the present invention implanted thereon.
Figure 6:
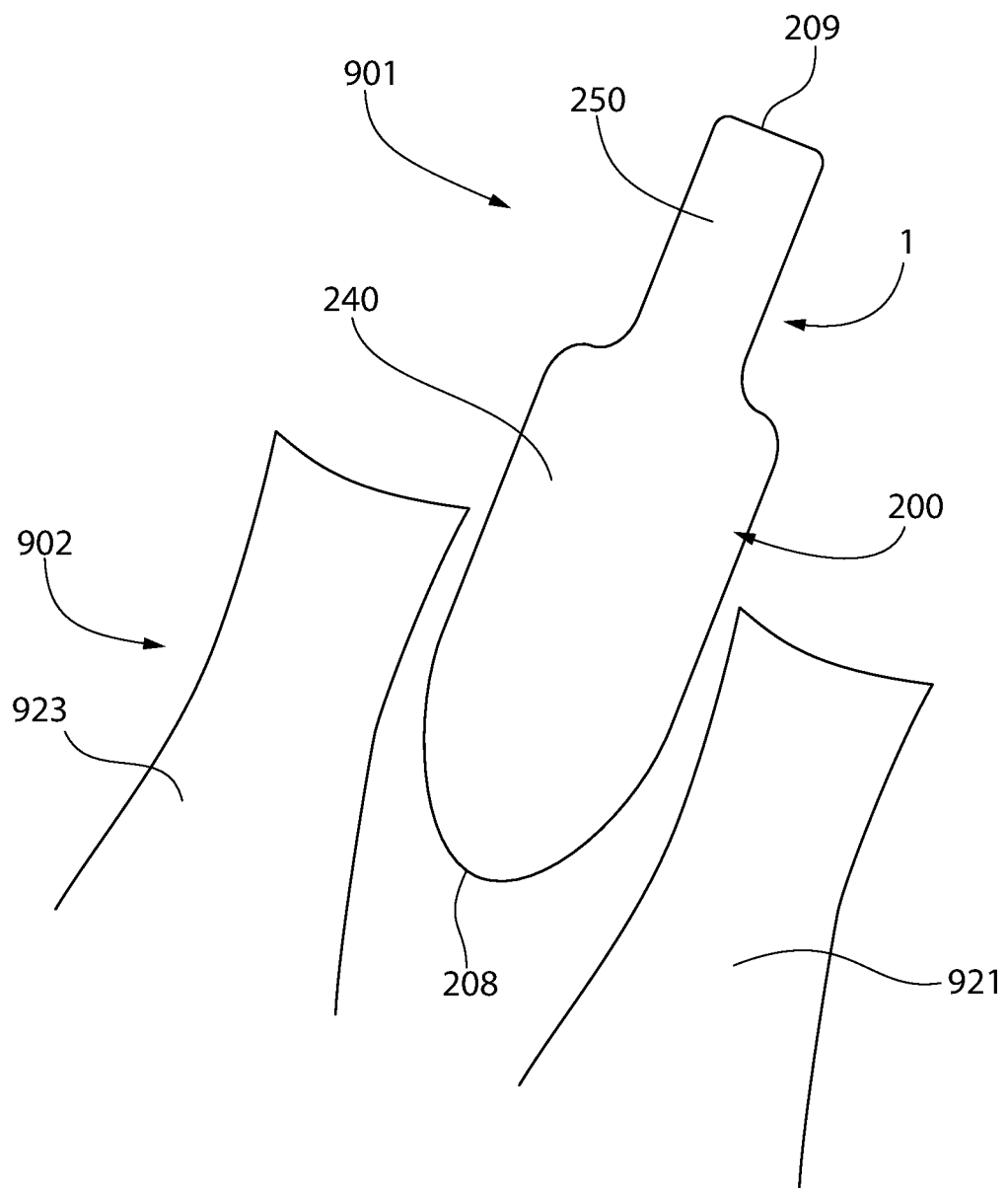
FIG. 6 is a close-up view of a portion of an eye comprising the treatment device of the present invention implanted thereon.
Figure 7:
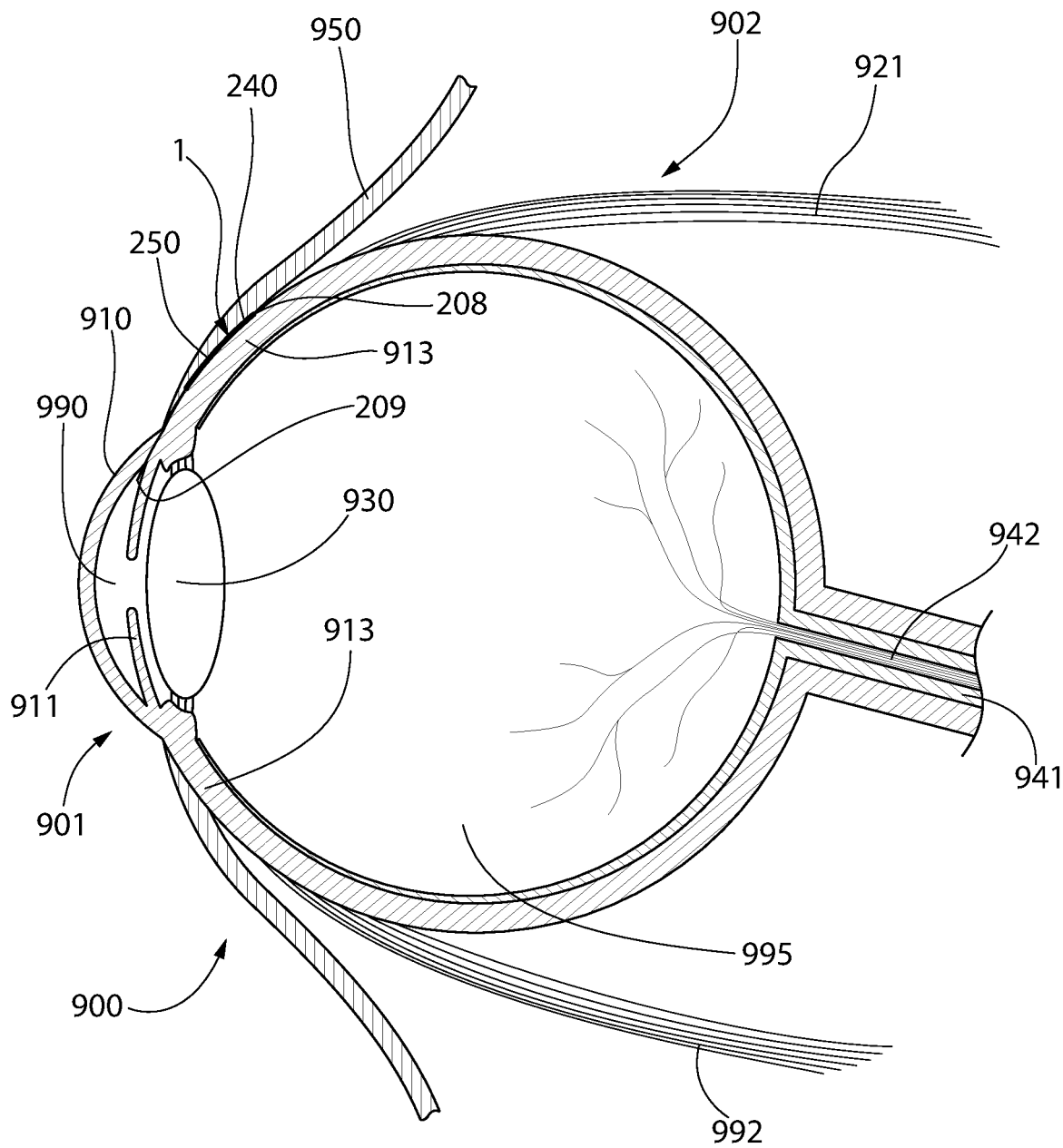
Figure 8:
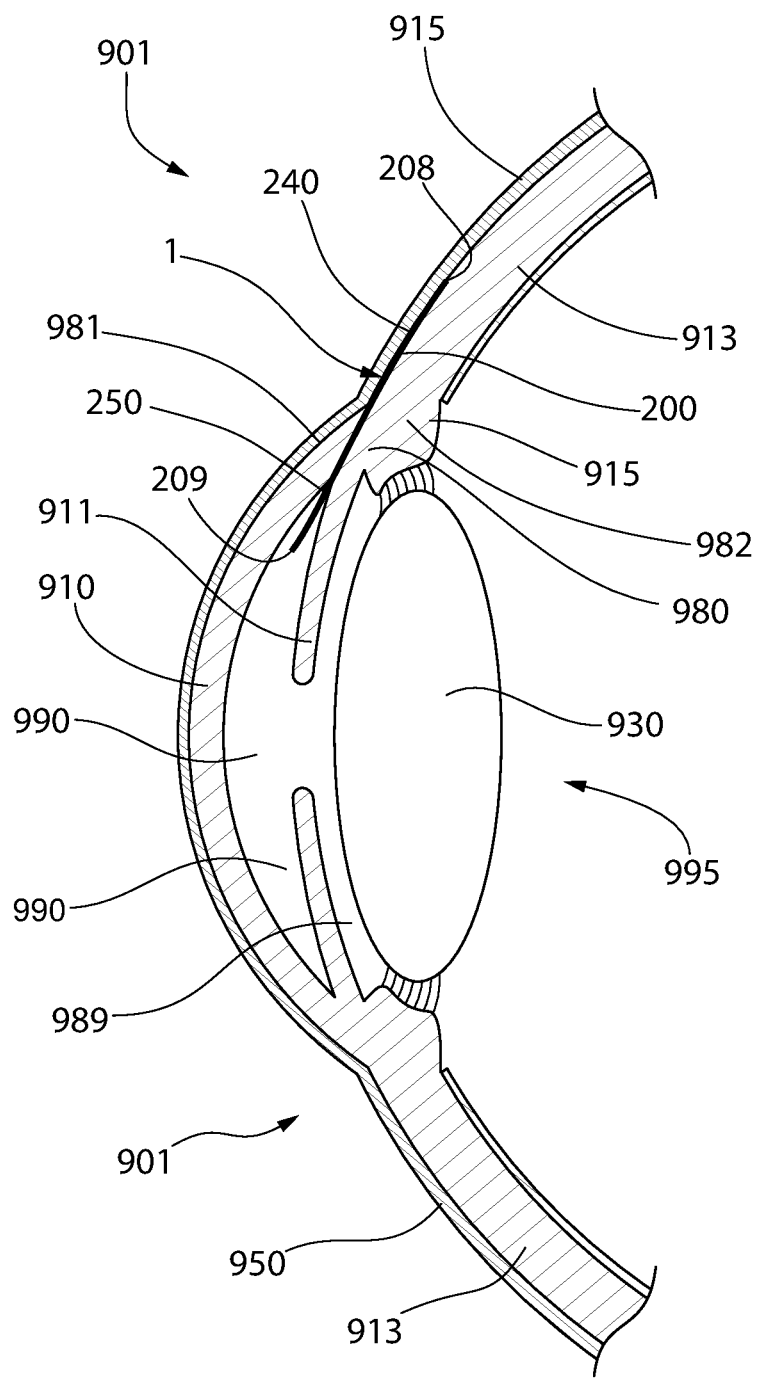
FIG. 8 is a close-up cross-sectional view the eye of FIG. 7 with the treatment device implanted there-on according to the present invention.

Referring to FIGS. 5 and 6, the treatment device 1 may be implanted onto an eye 900 such that the treatment device 1 is located at least partially between superior rectus muscle 921 and lateral rectus muscle 923. In such embodiments, the treatment device 1 may be located entirely between the superior rectus muscle 921 and lateral rectus muscle 923 such that there is no overlap the with the superior rectus muscle 921 or the lateral rectus muscle 923. In other embodiments, the treatment device 1 may be implanted onto an eye 900 such that the treatment device 1 is located at least partially between the inferior rectus muscle 922 and the lateral rectus muscle 923. In such embodiments, the treatment device 1 may be located entirely between the inferior rectus muscle 922 and lateral rectus muscle 923 such that there is no overlap with the inferior rectus muscle 923 or the lateral rectus muscle 923.

Referring now to FIGS. 18A-18F concurrently, multiple treatment devices 1d-1i are illustrated in accordance with another embodiment of the present invention. The devices 1d, 1e, 1f, 1g, 1h, 1i are similar to the device 1 except as described herein below. The description of the device 1 above generally applies to the devices 1d, 1e, 1f, 1g, 1h, 1i described below except with regard to the differences specifically noted below. A similar numbering scheme will be used for the devices 1d, 1e, 1f, 1g, 1h, 1i as with the device 1 except that a suffix of d, e, f, g, h, and i will be used.

As stated, the overall shape of the plate structure 200, 200d, 200e, 200f, 200g, 200h, 200i may be selected from a variety of geometries. Non-limiting examples of such geometries include polygonal shape, circular shape, mushroom shape, elliptic shape, oblong shape, oval shape, amoeba shape, or butterfly shape with lateral wings.

In a non-limiting embodiment, the treatment device 1d-1i, may comprise an extension portion 250d, 250e, 250f, 250g, 250h, 250i that is polygonal. According to these embodiments, the extension portion 250d, 250e, 250f, 250g, 250h, 250i may comprise a perimeter portion 255d, 255e, 255f, 255g, 255h, 255i that is comprised of substantially straight line portions, thereby forming the polygonal shape of the extension portion 250d, 250e, 250f, 250g, 250h, 250i. The perimeter portion 255d, 255e, 255f, 255g, 255h, 255i of the extension portion 250d, 250e, 250f, 250g, 250h, 250i forms part of the perimeter 203d, 203e, 203f, 203g, 203h, 203i of the plate structure 200d, 200e, 200f, 200g, 200h, 200i.

Figure 18A:
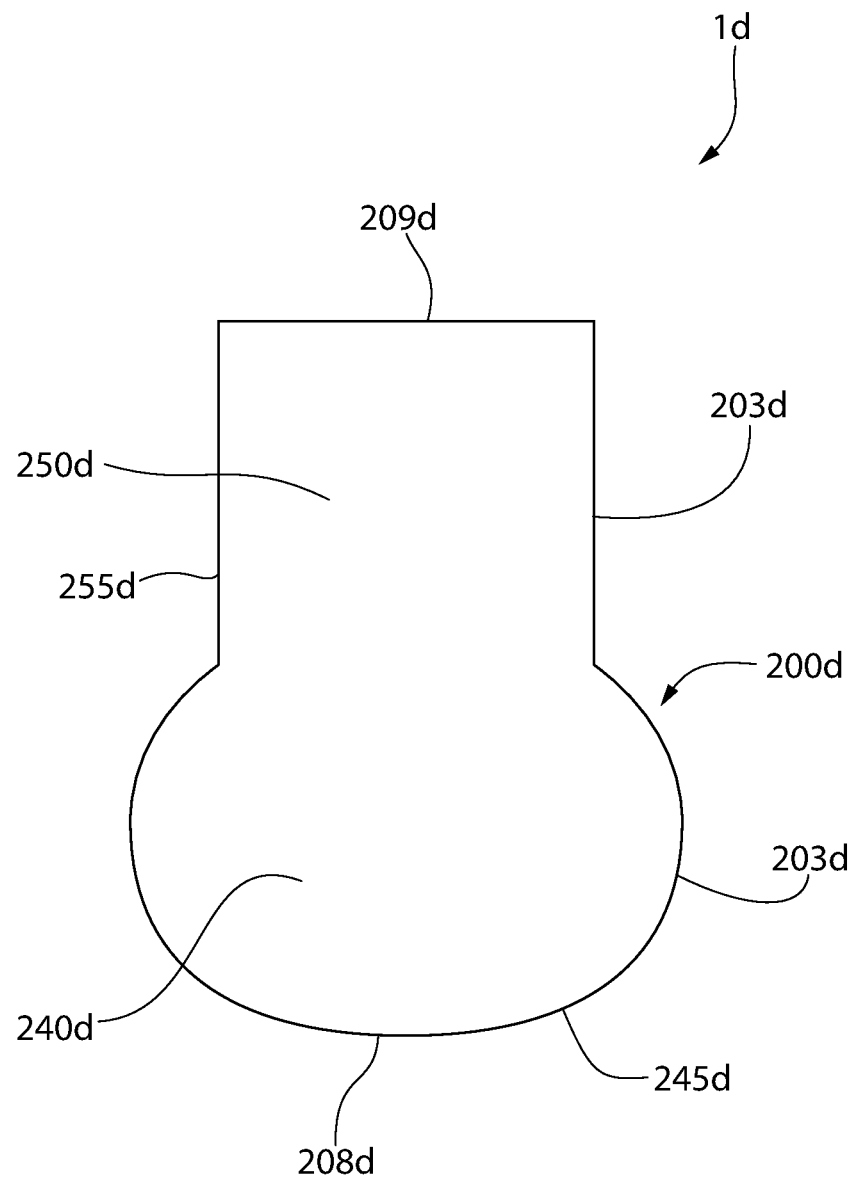
FIG. 18A is a top view of a treatment device according to another embodiment of the present invention.
Figure 18B:
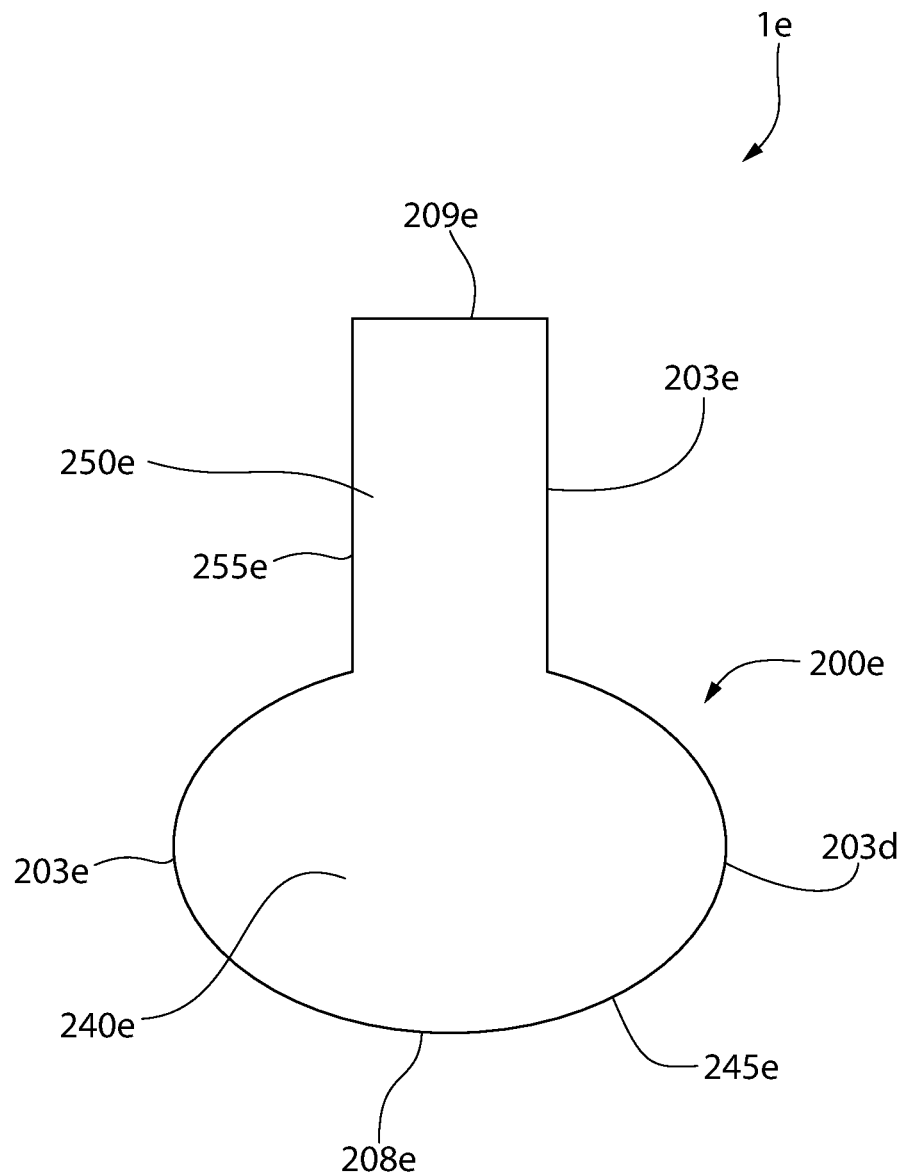
FIG. 18B is a top view of a treatment device according to another embodiment of the present invention.
Figure 18C:
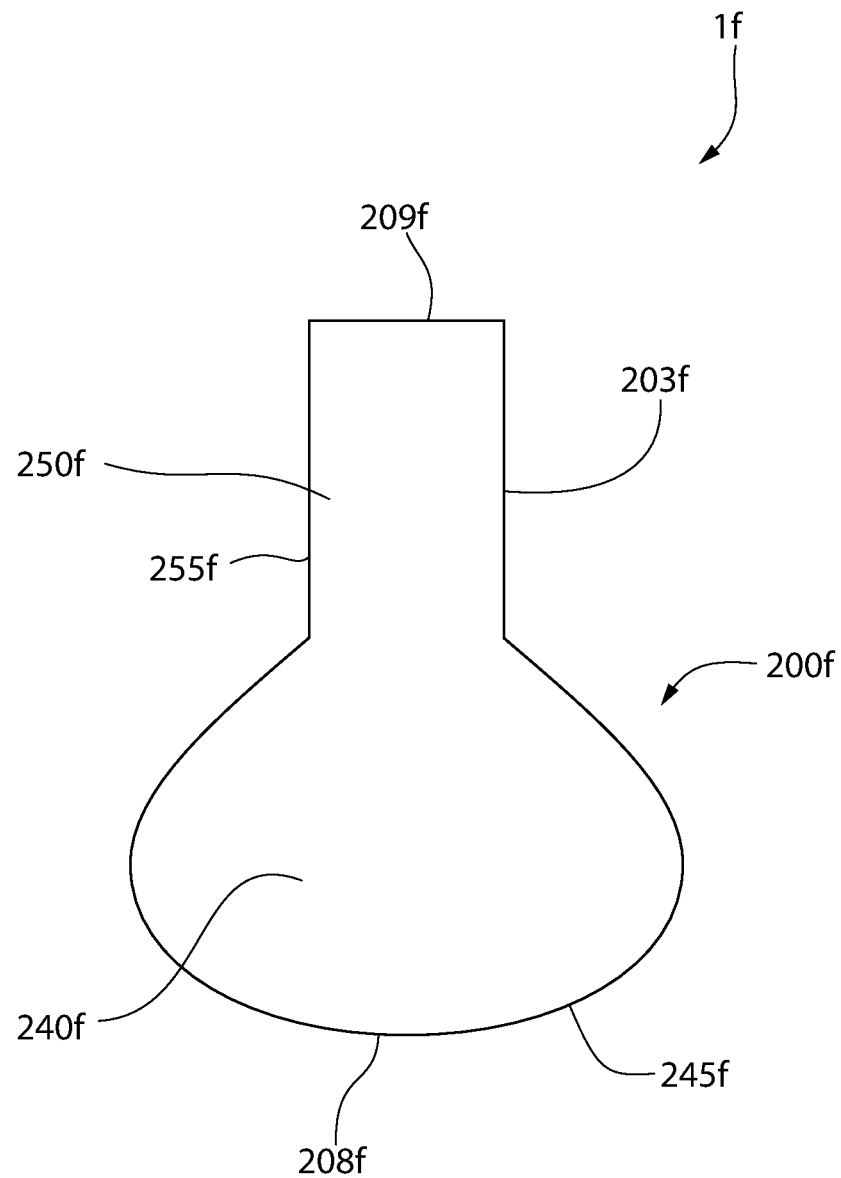
FIG. 18C is a top view of a treatment device according to another embodiment of the present invention.
Figure 18D:
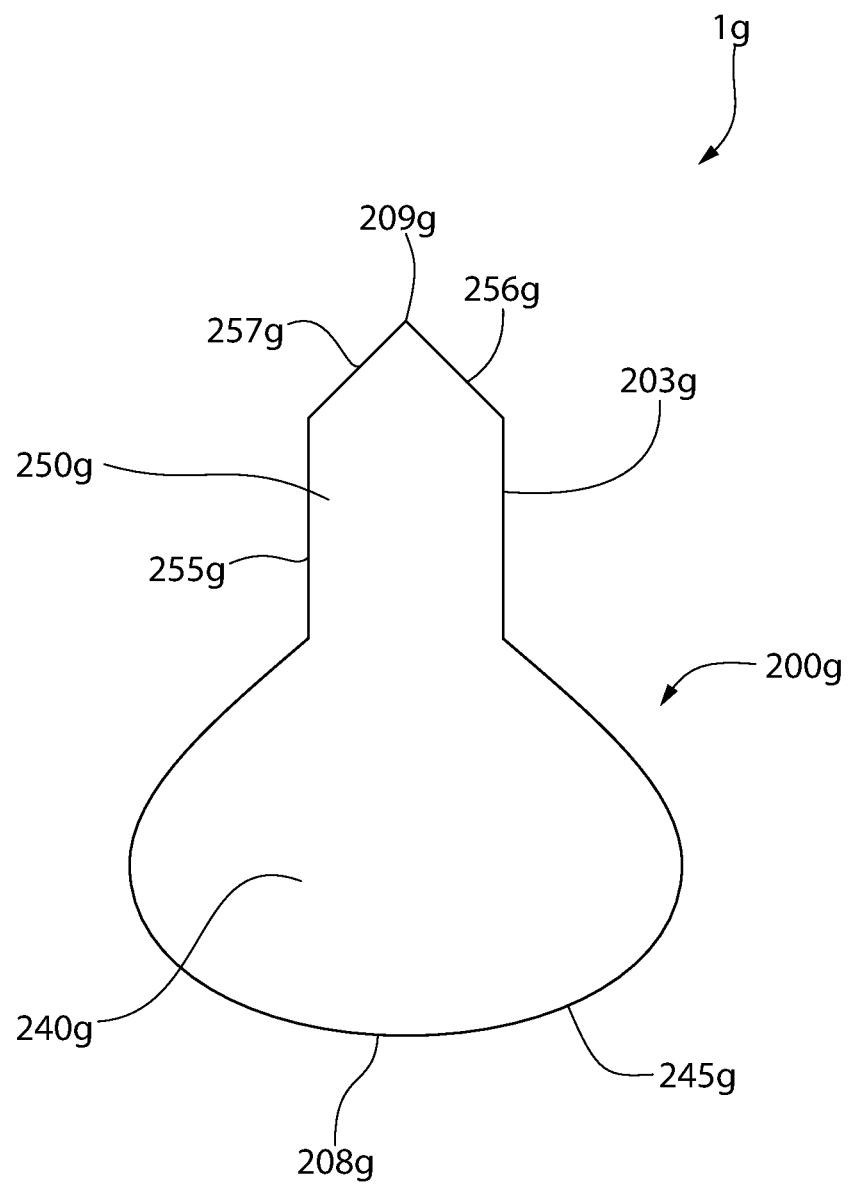
FIG. 18D is a top view of a treatment device according to another embodiment of the present invention.
Figure 18E:
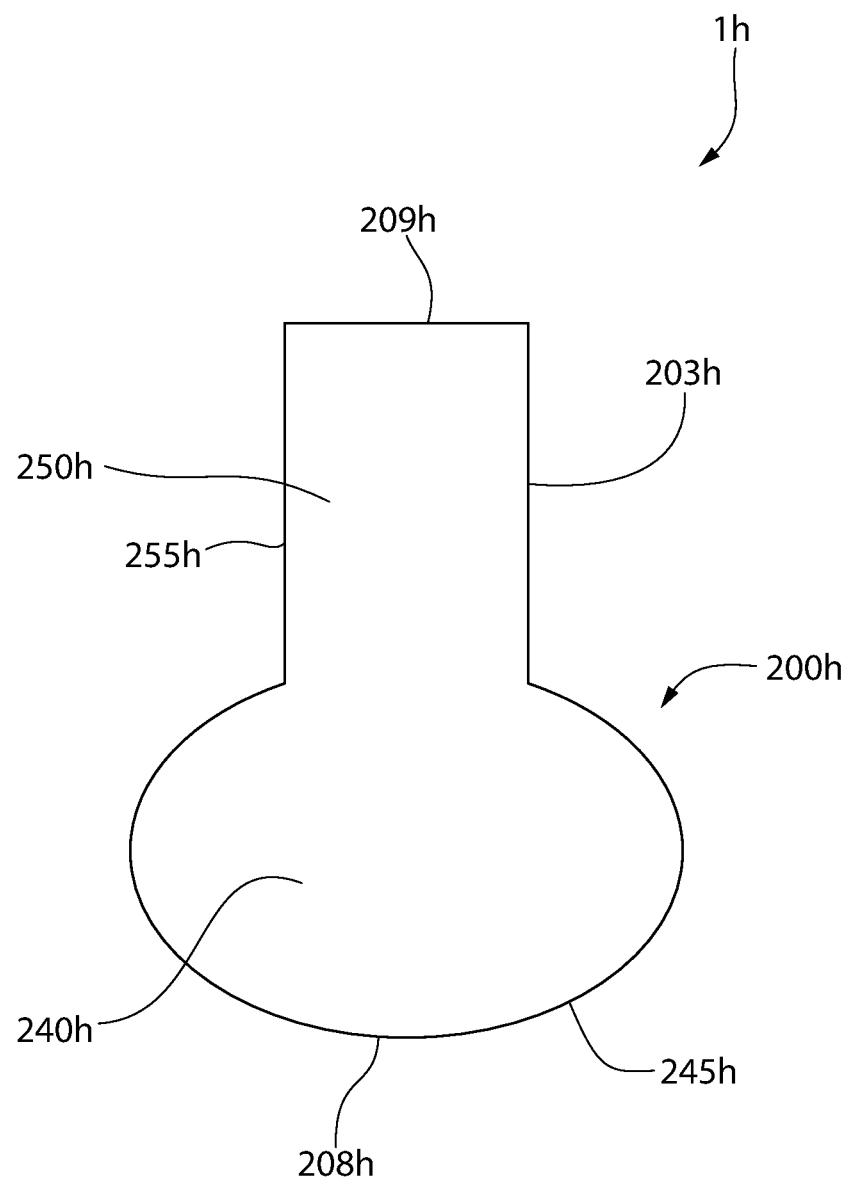
FIG. 18E is a top view of a treatment device according to another embodiment of the present invention.

In a non-limiting embodiment, the perimeter portion 255d, 255e, 255f, 255g, 255h, 255i of the extension portion 250d, 250e, 250f, 250g, 250h, 250i may form a portion of a rectangle, square, or triangle. Referring to FIG. 18D in particular, the extension portion 250g may comprise a rectangular portion and a triangular tip 256g terminating at an apex 257g, whereby the apex 257g coincides with the distal end 209g of the treatment device 1g. Although not shown, the perimeter portion 255d, 255e, 255f, 255g, 255h, 255i of the extension portion 250d, 250e, 250f, 250g, 250h, 250i may be curved or non-polygonal. In other embodiments, the distal end 209d, 209e, 209f, 209h, and 209i may comprise a perimeter portion 255d, 255e, 255f, 255h, 255i that is formed from a straight line.

In a non-limiting embodiment, the treatment device 1d-1i, may comprise a main body portion 240d, 240e, 240f, 240g, 240h, 240i comprising a perimeter portion 245d, 245e, 245f, 245g, 245h, 245i. The perimeter portion 245d, 245e, 245f, 245g, 245h, 245i of the main body portion 240d, 240e, 240f, 240g, 240h, 240i forms part of the perimeter 203d, 203e, 203f, 203g, 203h, 203i of the plate structure 200d, 200e, 200f, 200g, 200h, 200i.

The perimeter portion 245d, 245e, 245f, 245g, 245h, 245i of the main body portion 240d, 240e, 240f, 240g, 240h, 240i intersects the perimeter portion 255d, 255e, 255f, 255g, 255h, 255i of the extension portion 250d, 250e, 250f, 250g, 250h, 250i.

In a non-limiting embodiment, the perimeter portion 245d, 245e, 245f, 245g, 245h, 245i of the main body portion 240d, 240e, 240f, 240g, 240h, 240i may be curved or non-polygonal in shape. Referring to FIG. 18C in particular, the perimeter portion 245f, 245g of the main body portion 240f, 240g may comprise both straight segments and a curved segment, whereby the straight segments intersect with the perimeter portion 255f, 255g of the extension portion 250f, 250g. The proximal end 208d, 208e, 208f, 208g, 208h, and 208i may comprise a perimeter portion 245d, 245e, 245f, 245h, 245i that is formed from a curved line.

The curved shape of the perimeter portion 245d, 245e, 245f, 245g, 245h, 245i of the main body portion 240d, 240e, 240f, 240g, 240h, 240i may be perfectly circular or ovular.

Figure 18F:
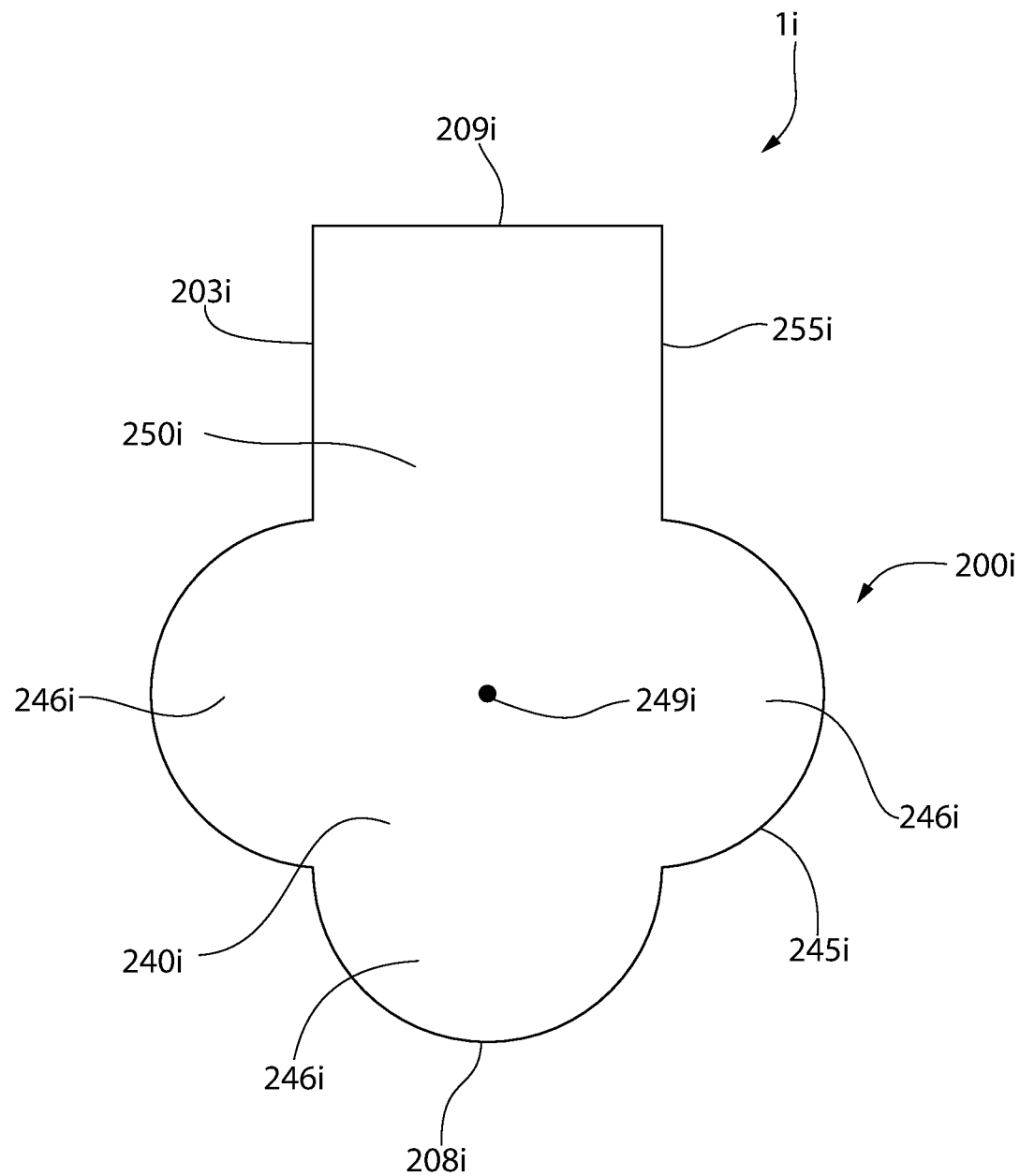
FIG. 18F is a top view of a treatment device according to another embodiment of the present invention.

Referring now to FIG. 18F, the treatment device 1i may have a main-body portion 240i comprising a multi-lobed geometry. Specifically, the main body portion 240i may comprise two or more lobes 246i extending outward and forming part of the perimeter portion 245i of the main body portion 240i. Each lobe 246i may comprise a portion of a circular shape—i.e., a portion of a circle, a portion of an oval. Each lobe may be a symmetrical shape or asymmetrical shape. Each of the lobes 246i may be oriented symmetrically about a central point 249i on the main body portion 240i.

In a non-limiting example, the multi-lobed geometry of the main-body portion 240i may be a trilobed geometry. The multi-lobed geometry may increase the surface area of the treatment device 1i while avoiding the eye muscles, such that two lobes are in front of the eye muscles and the third lobe extends to the back of the eye, in between the eye muscles. Such increased surface may be advantageous for fluid absorption in lowering intraocular pressure. According to the embodiments where the multi-lobed geometry is trilobed, the main-body portion 240i may have a generally triangular shape—whereby the corners may be rounded.

Figure 9:
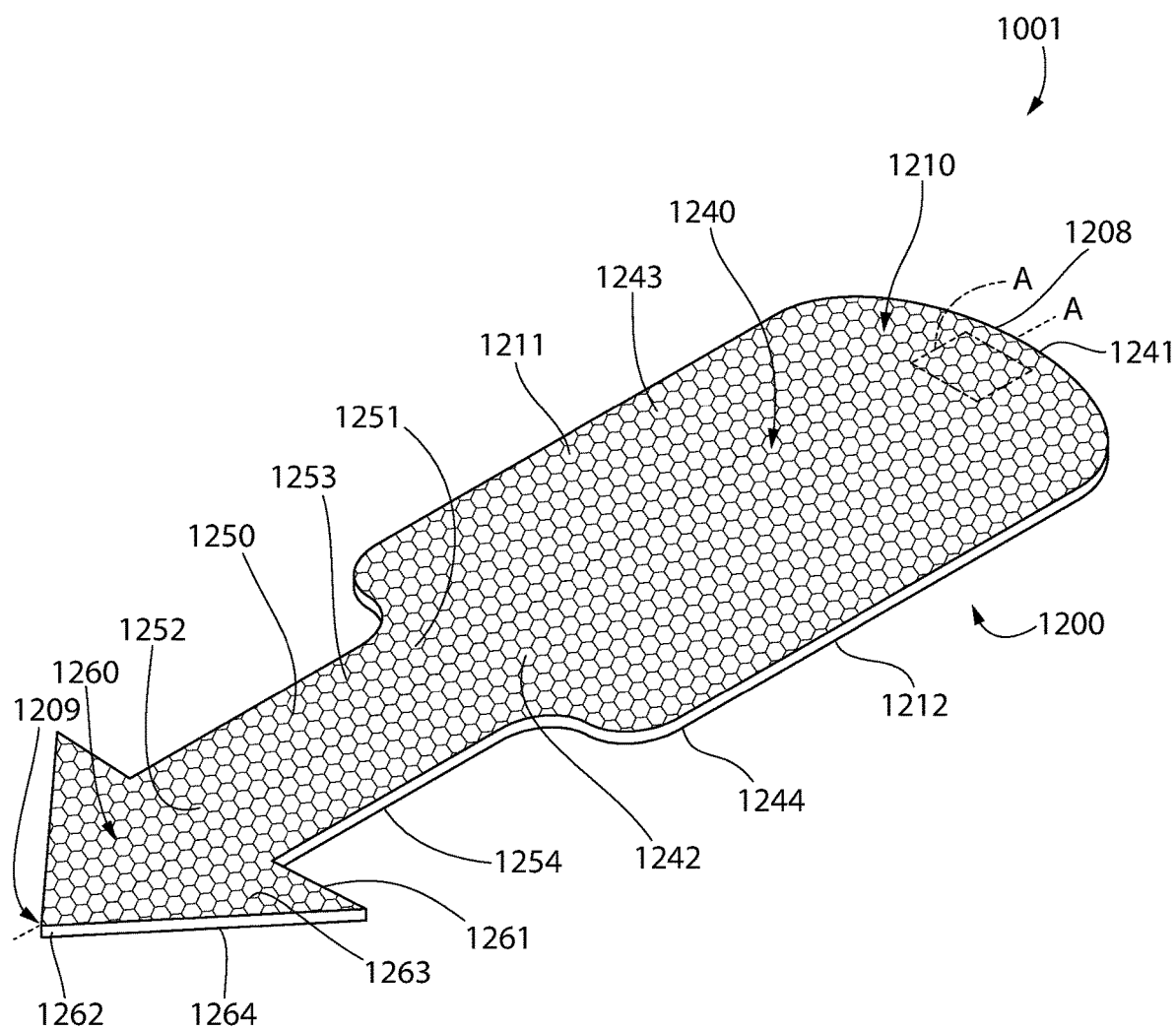
FIG. 9 is a perspective view of a treatment device according to another embodiment of the present invention.
Figure 10:
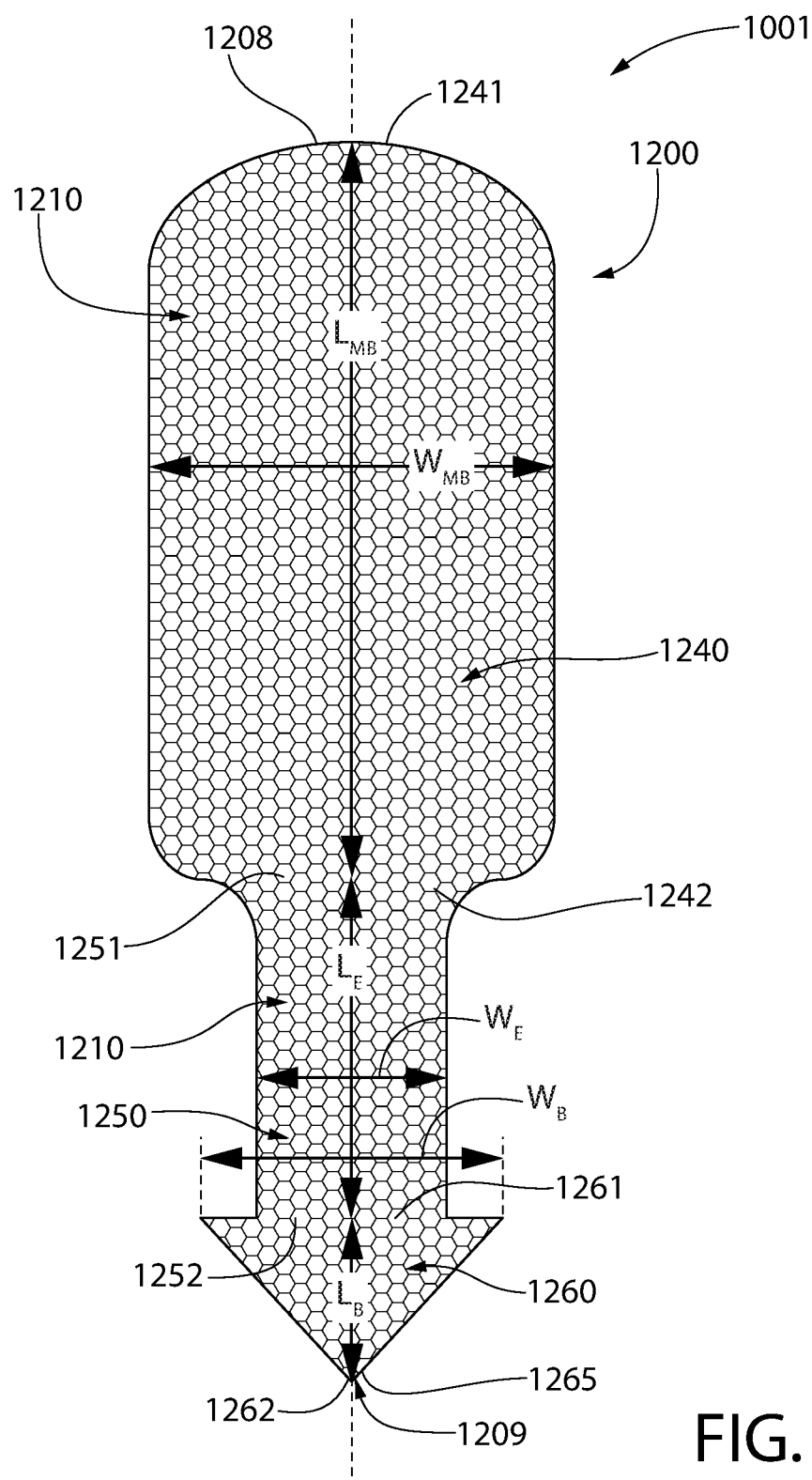
FIG. 10 is a top view of the treatment device of FIG. 9.

Referring now to FIGS. 9 and 10, a treatment device 1001 is illustrated in accordance with another embodiment of the present invention. The device 1001 is similar to the device 1 except as described herein below. The description of the device 1 and 1d-1i above generally applies to the device 1001 described below except with regard to the differences specifically noted below. A similar numbering scheme will be used for the device 1001 as with the devices 1, 1d-1i except that a 1000-series number will be used.

The device 1001 may comprise a main body portion 1240, an extension portion 1250, and further comprise a barb portion 1260. The barb portion 1260 may comprise a proximal end 1261 that is opposite a distal end 1262. The proximal end 1261 of the barb portion 1260 may extend from the distal end 1252 of the extension portion 1240. According to this embodiment, the distal end 1262 of the barb portion 1260 may overlap with the distal end 1209 of the plate structure 1200. The longitudinal axis A-A may intersect both the proximal end 1261 and the distal end 1262 of the barb portion 1260.

The barb portion 1260 may comprise a first major surface 1263 that is opposite a second major surface 1264. The first major exposed surface 1201 of the plate structure 1200 may comprise the first major surface 1263 of the barb portion 1260. The second major exposed surface 1202 of the plate structure 1200 may comprise the second major surface 1264 of the barb portion 1260.

The barb portion 1260 may extend a barb length $L_B$ that spans the distance from the proximal end 1261 to the distal end 1262 of the barb portion 1260. The barb length $L_B$ may range from about 1 mm to about 3 mm—including all lengths and sub-ranges there-between. In a preferred embodiment, the barb length $L_B$ may be about 2 mm.

The barb portion 1260 may have a maximum barb width $W_B$ that as measured by the maximum distance spanning the direction extending normal to the longitudinal axis A-A. The maximum barb width $W_B$ may range from about 1.0 mm to about 54.0 mm—including all lengths and sub-ranges there-between. In a preferred embodiment, the maximum barb width $W_B$ may be about 3.6 mm.

The maximum barb with $W_B$ may be greater than the extension width $W_E$. In some embodiments, a ratio of the maximum barb width $W_B$ to the extension width $W_E$ may range from about 1.01:1 to about 3:1—including all ratios and sub-ranges there-between. In some embodiments, the ratio of the barb width $W_B$ to the extension width $W_E$ may range from about 1.1:1 to about 2:1—including all ratios and sub-ranges there-between. In a preferred embodiment, the ratio of the barb width $W_B$ to the extension width $W_E$ may be about 1.4:1.

The first major surface 1263 of the barb portion 1260 may be substantially coplanar with the first major surface 1253 of the extension portion 1250. The second major surface 1264 of the barb portion 1260 may be substantially coplanar with the second major surface 1254 of the extension portion 1250.

The barb portion 1260 may have a height, as measured by the distance between the first and second major surfaces 1263, 1264 of the barb portion 1260, that is substantially equal to the first height $H_1$ of the plate structure 1200. The barb portion 1260 may comprise a triangular configuration comprising an apex point 1265. The apex point 1265 may overlap with the distal end 1209 of the plate structure 1200.

Figure 11:
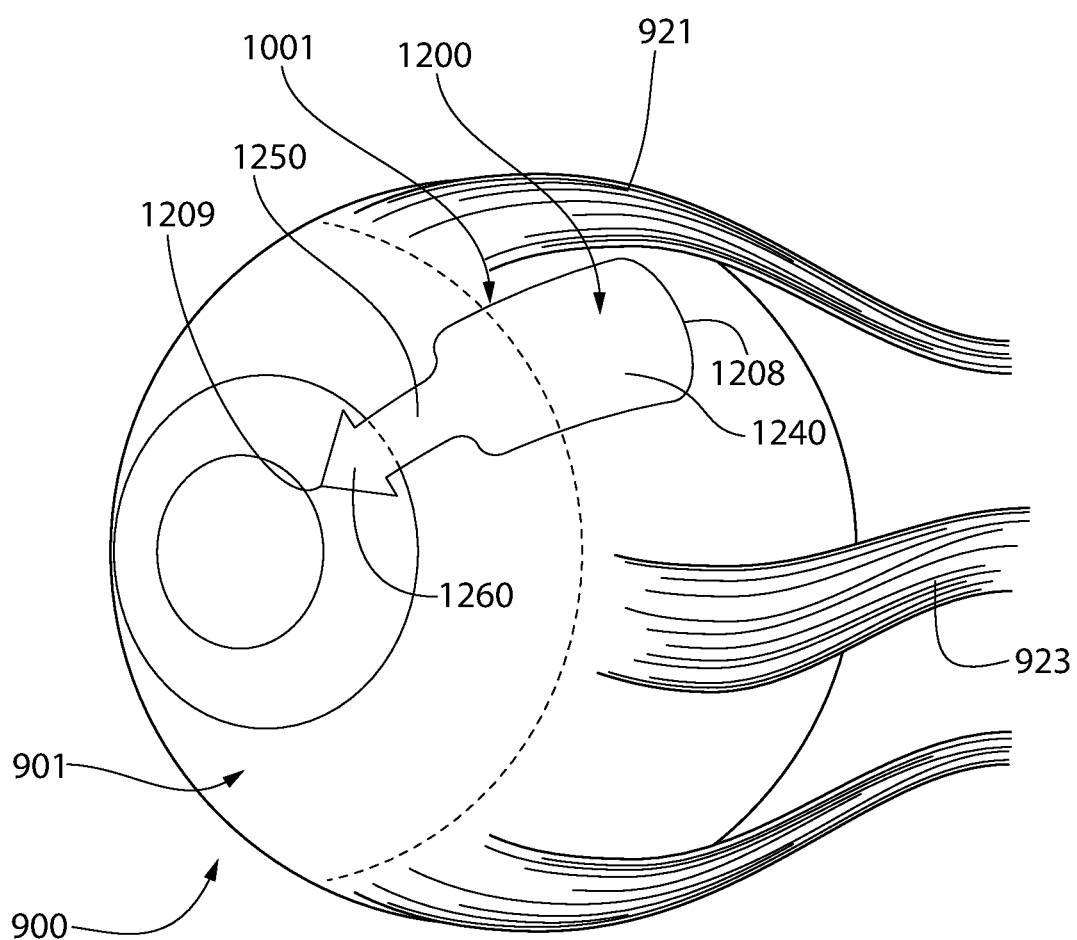
FIG. 11 is a perspective anterior view of an eye comprising the treatment device of FIG. 9 implanted thereon.
Figure 12:
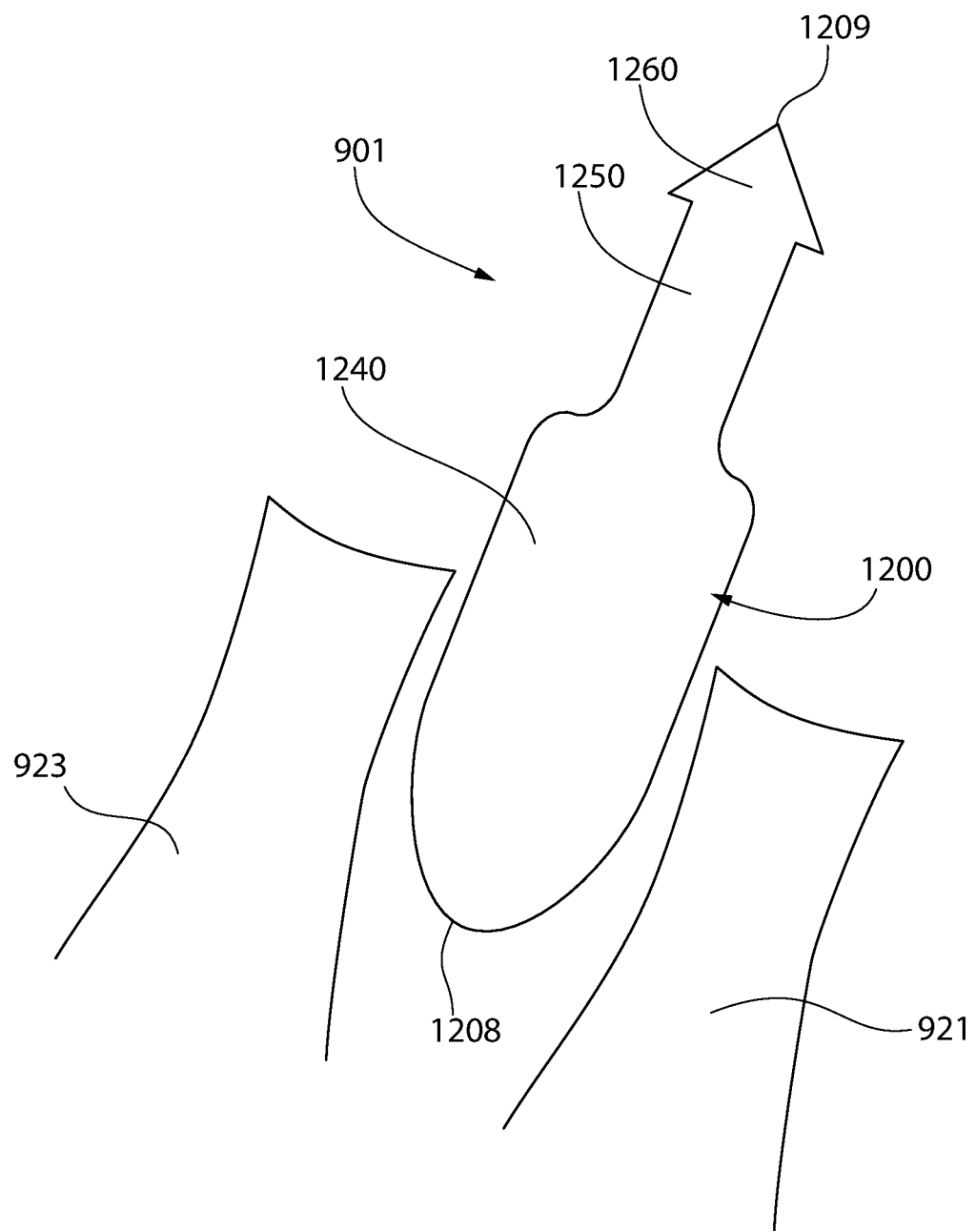
FIG. 12 is a close-up view of a portion of an eye comprising the treatment device of FIG. 9 implanted thereon.
Figure 14:
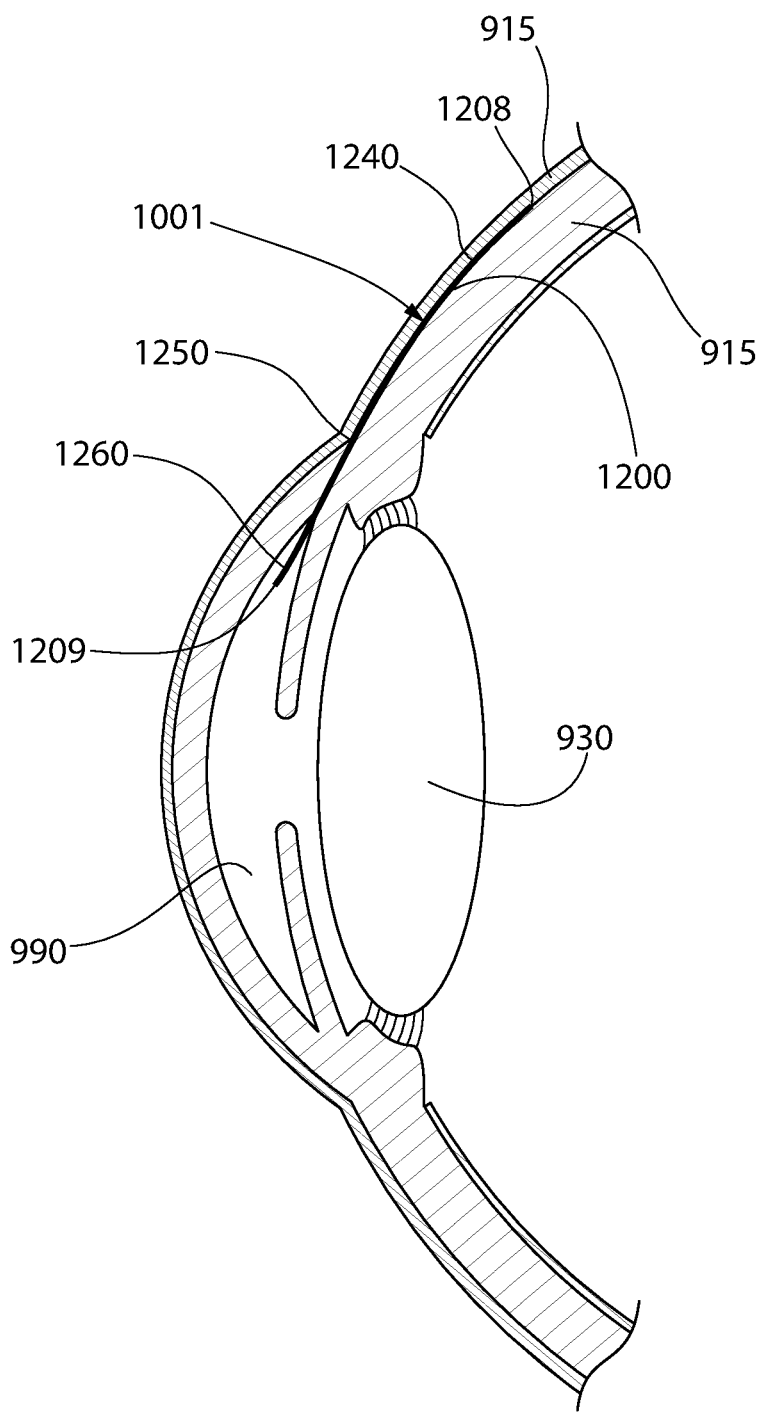
FIG. 14 is a close-up cross-sectional view the eye of FIG. 11 with the treatment device of FIG. 9 implanted thereon.

Referring now to FIGS. 11, 12, and 14, the treatment device 1001 provides such fluid pathway for excess fluid to exit the eye 900. Specifically, the treatment device 1 may be implanted onto the eye 900 such that it creates a fluid pathway from the anterior chamber 990 to the exterior of the sclera 913 to form a bleb. Once on the exterior surface of the sclera 913, the excess fluid can be carried away from the eye 900 by absorption into surrounding tissue in the subject.

In particular, the treatment device 1001 may be implanted onto the eye 900 such that the plate structure 1200 is located between the sclera 913 and conjunctiva 950 tissue. The barb portion 1260 may extend from the extension portion 1250 through the sclera 913 and into the anterior chamber 990 of the eye 900 such that the distal end 1209 of the plate structure 200 is located within the anterior chamber 990.

Figure 13:
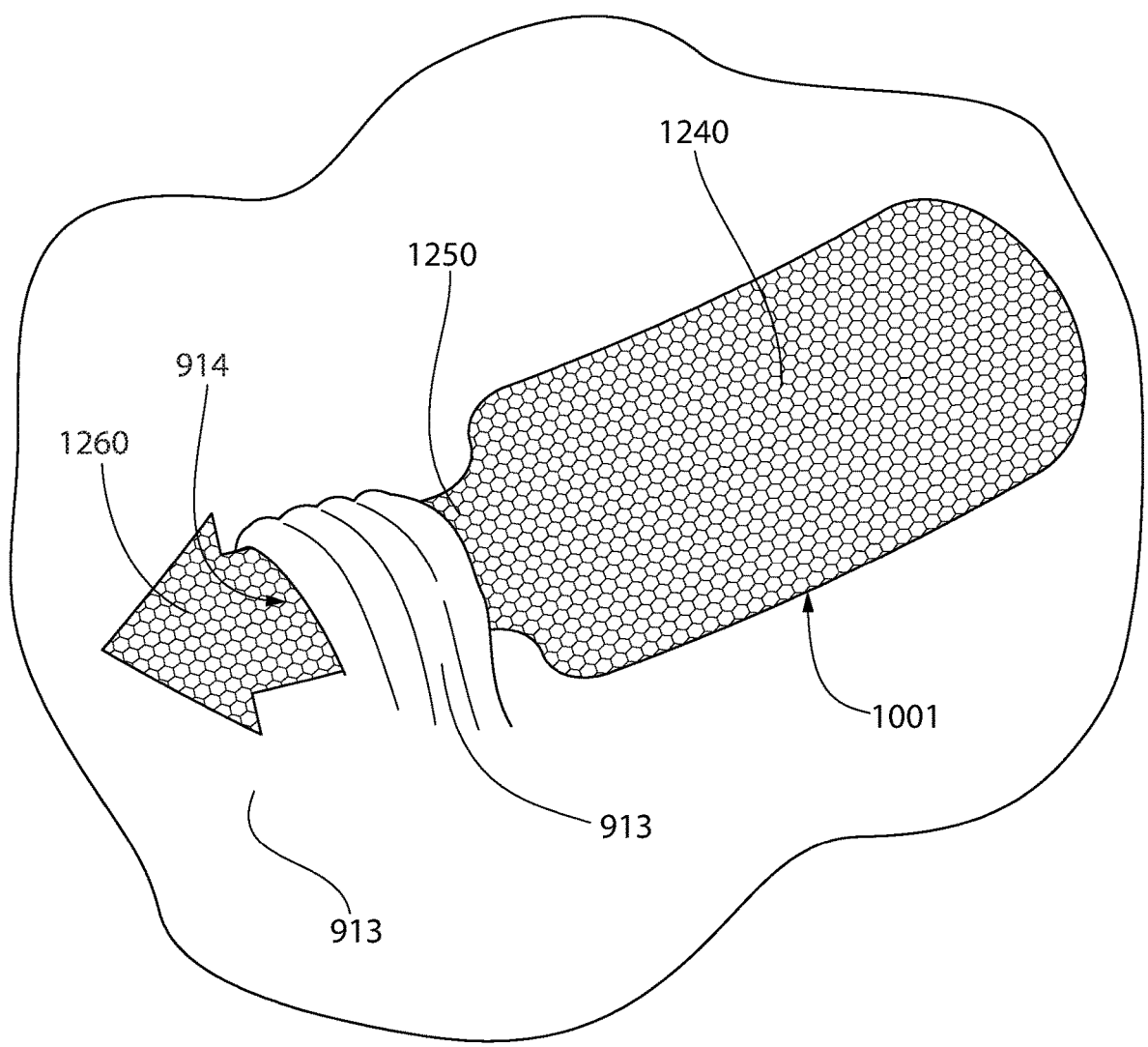
FIG. 13 is another close-up view of a portion of an eye comprising the treatment device of FIG. 9 implanted thereon.

Referring now to FIG. 13, a portion of the sclera 913 may be cut to form a slit 914 and that the barb portion 1260 may be inserted through the slit 914, thereby anchoring the device 1 to the sclera 913. The slit 913 may have a width substantially equal to the extension portion width $W_E$ such that the barb portion 1260 and main body portion 1240 abut sclera tissue 913 surrounding the slit 914 and the extension portion 1250 is anchored inside of the slit beneath sclera tissue 913. Implanting the device 1001 according to this embodiment may be performed by temporarily deforming the barb portion 1260 such that is has a reduced barb width $W_B$ that is equal to or less than the width of the slit 914, allowing the barb portion 1260 to enter the slit 914. Once past the slit 914, the barb portion 1260 can then un-deform such that the barb portion 1260 has the barb width $W_B$ in an undeformed state.

Figure 15:
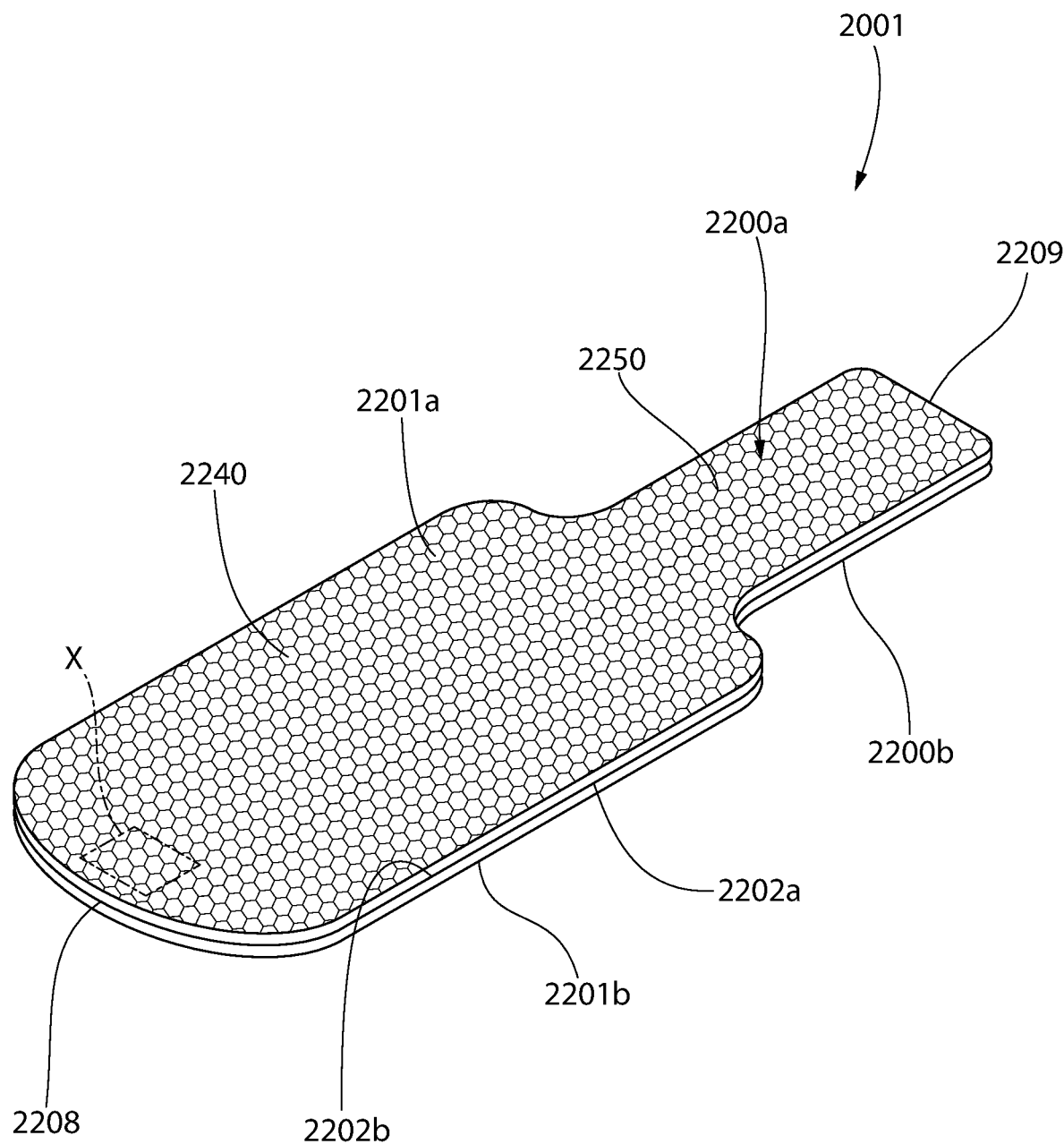
FIG. 15 is a perspective view of a treatment device according to another embodiment of the present invention.
Figure 16:
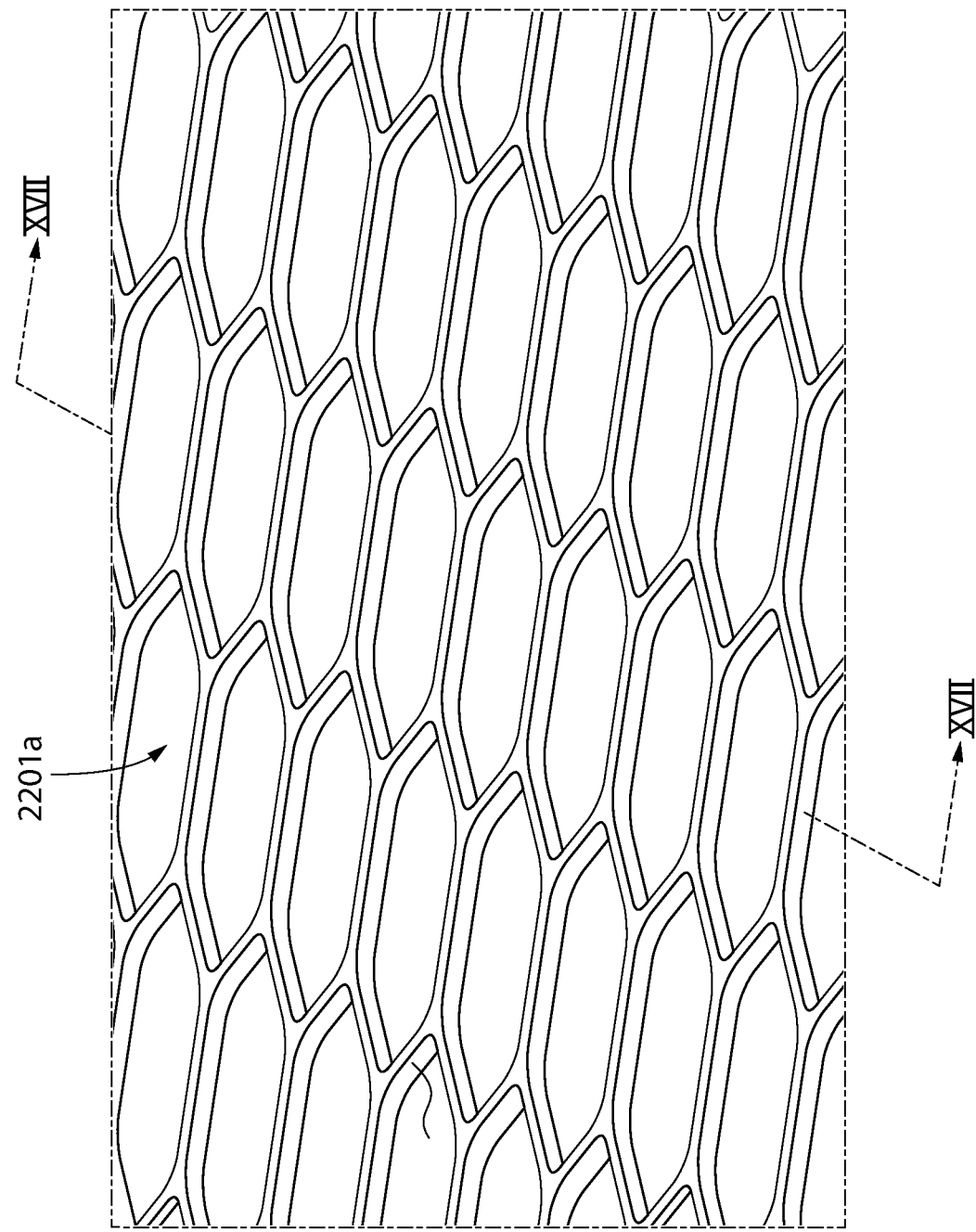
FIG. 16 is a close-up view of the treatment device according to section X identified in FIG. 15.
Figure 17:
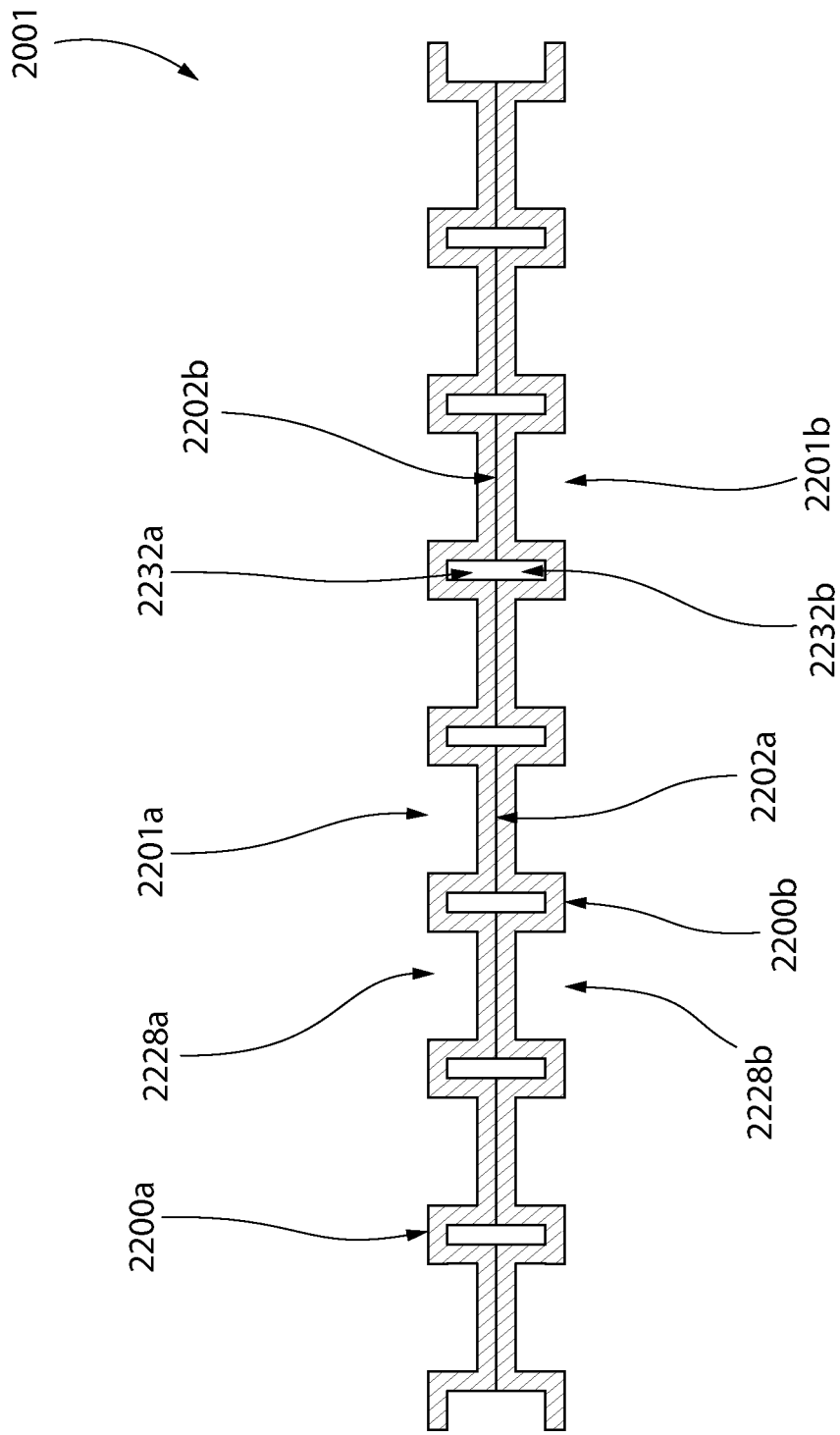
FIG. 17 is a cross-sectional view of the treatment device shown along line XVII-XVII in FIG. 16.

Referring now to FIGS. 15-17, a treatment device 2001 is illustrated in accordance with another embodiment of the present invention. The device 2001 is similar to the devices 1, 1001 except as described herein below. The description of the devices 1, 1d-1i, and 1001 above generally applies to the device 2001 described below except with regard to the differences specifically noted below. A similar numbering scheme will be used for the device 2001 as with the devices 1, 1d-1i, 1001 except that a 2000-series number will be used.

The device 2001 may comprise a plurality of plate structures 2200. Although not limited to two plate structures, the foregoing discussion will refer to a first plate structure 2200a and a second plate structure 2200b. The description of the plate structure 200, 1200 above generally applies to the first plate structure 2200a and the second plate structure 2200b described below except with regard to the differences specifically noted below. A similar numbering scheme will be used for the first plate structure 2200a as with the plate structures 200, 1200 except that a 2000-series number and an a-suffix will be used. A similar numbering scheme will be used for the second plate structure 2200b as with the plate structures 200, 1200 except that a 2000-series number and a b-suffix will be used.

The device 2001 may comprise the first plate structure 2200a and the second plate structure 2200b stacked together. As demonstrated in FIG. 17, the second major surface 2202a of the first plate structure 2200a may face the second major surface 2202b of the second plate structure 2200b. The second major surface 2202a of the first plate structure 2200a may be in direct contact with the second major surface 2202b of the second plate structure 2200b. In other embodiments, the device of this embodiment may comprise one or more intermediate layers positioned between the second major surface 2202a of the first plate structure 2200a and the second major surface 2202b of the second plate structure 2200b. Non-limiting examples of additional intermediate layers include adhesives, pharmacological layers, as well as additional multi-directional plates according to the present invention.

The second major surface 2202a of the first plate structure 2200a may face the second major surface 2202b of the second plate structure 2200b such that the open-channels 2232a present on the second major surface 2202a of the first plate structure 2200a mirror the open channels 2232b that are present on the second major surface 2202b of the second plate structure 2200b. The term "mirror" refers to the open-ends of each open-channels 2232a, 2232b completely overlapping each other such that, together, the combination of open-channels 2232a, 2232b of the first and second plate structures 2200a, 2200b form a collectively closed channel. In this manner, the treatment device 2001 may be a composite structure having insulating properties.

Although not pictured, in other embodiments, the second major surface 2202a of the first plate structure 2200a may face the second major surface 2202b of the second plate structure 2200b such that the open-channels 2232a present on the second major surface 2202a of the first plate structure 2200a are horizontally offset from the open channels 2232b that are present on the second major surface 2202b of the second plate structure 2200b. The term "horizontally offset" refers to the open-ends of each open-channels 2232a, 2232b either only partially overlapping or the open-ends of each open-channels 2232a, 2232b not overlapping at all.

Although not pictured, other embodiments provide that the second major surface 2202a of the first plate structure 2200a may face the first major surface 2201b of the second plate structure 2200b such that the open-channels 2232a present on the second major surface 2202a of the first plate structure 2200a face the open cells 2228b that are present on the first major surface 2201b of the second plate structure 2200b. In other embodiments, the first major surface 2201a of the first plate structure 2200a may face the second major surface 2202b of the second plate structure 2200b such that the open-cells 2228a present on the first major surface 2201a of the first plate structure 2200a face the open channels 2232b that are present on the second major surface 2202b of the second plate structure 2200b.

Although not pictured, in other embodiments, the first major surface 2201a of the first plate structure 2200a may face the first major surface 2201b of the second plate structure 2200b such that the open-cells 2228a present on the first major surface 2201a of the first plate structure 2200a mirror the open-cells 2228b that are present on the first major surface 2201b of the second plate structure 2200b. The term "mirror" refers to the open-cells 2228a, 2228b completely overlapping each other such that, together, the combination of open-cells 2228a, 2228b of the first and second plate structures 2200a, 2200b form a collectively closed cell. In this manner, the treatment device 2001 may be a composite structure having insulating properties.

Although not pictured, in other embodiments, the first major surface 2201a of the first plate structure 2200a may face the first major surface 2201b of the second plate structure 2200b such that the open-cells 2228a present on the first major surface 2201a of the first plate structure 2200a are horizontally offset from the open-cells 2228b that are present on the first major surface 2201b of the second plate structure 2200b. The term "horizontally offset" refers to the open-ends of each open-cell 222a, 2228b either only partially overlap or do not overlap at all.

The device 2001 according to this embodiment may be formed by manufacturing each of the first and second plate structures 2200a, 2200b separately followed by manually stacking the first and second plate structures 2200a, 2200b together. Alternatively, two or more plates structures can be fabricated in a pre-stacked arrangement. The device 2001 according to this embodiment may be formed by photolithographic or etching process that forms the stacked plate structure.

Figure 19:
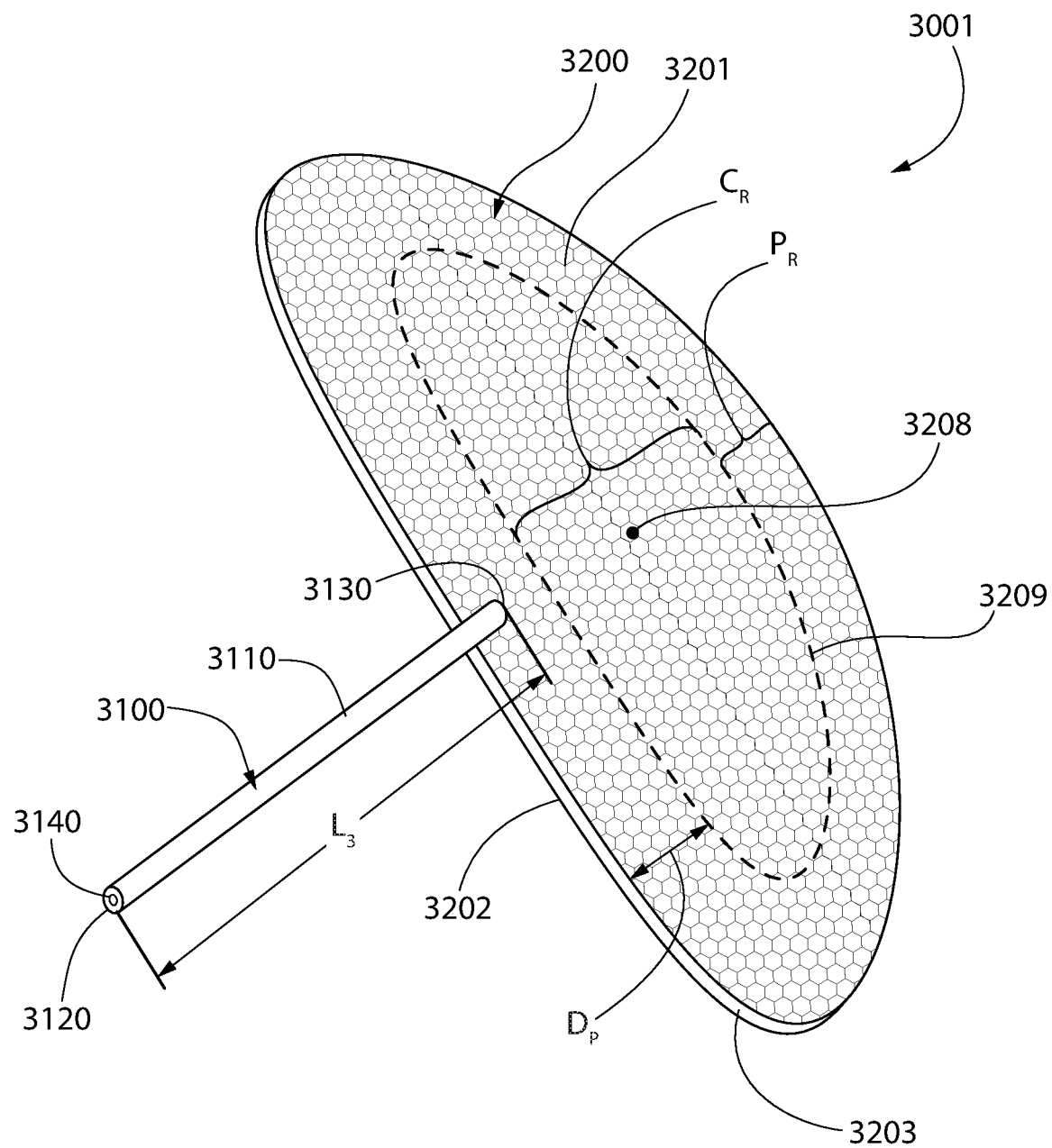
FIG. 19 is a perspective view of a treatment device according to another embodiment of the present invention.
Figure 20:
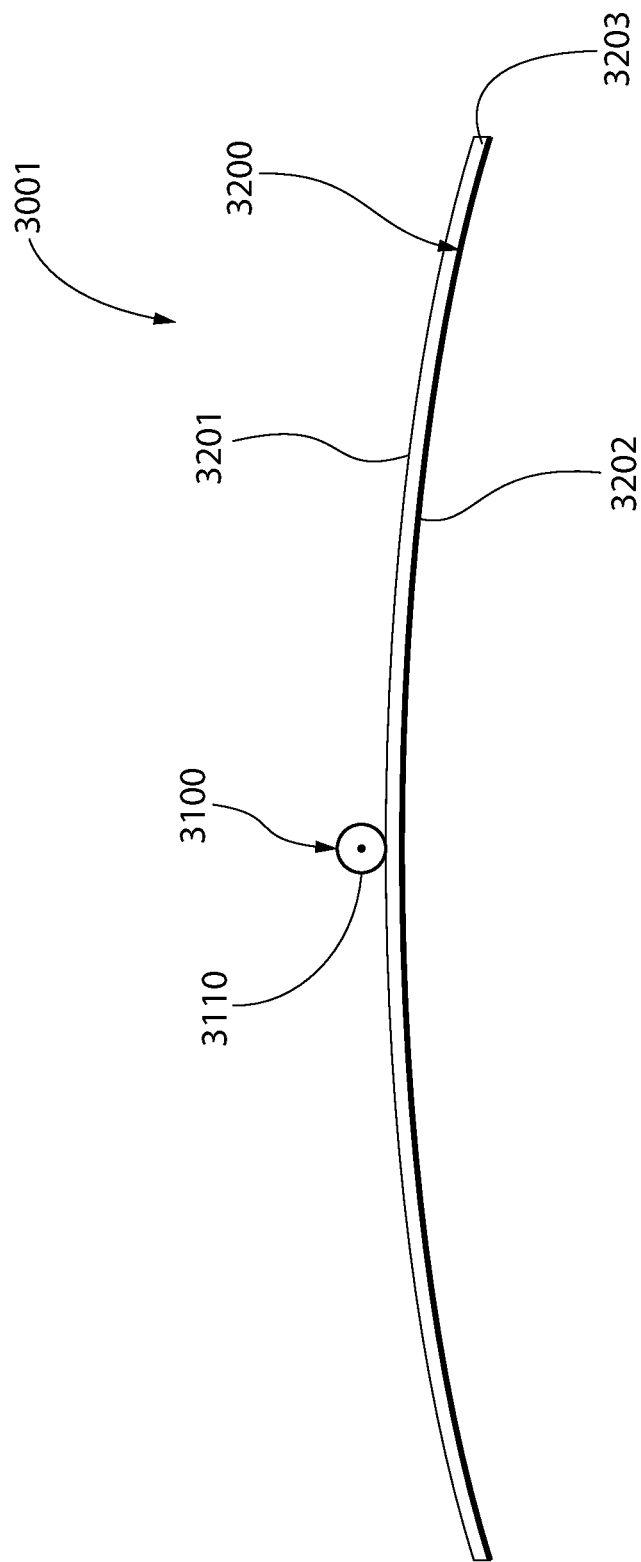
FIG. 20 is a side view of the treatment device of FIG. 19.

Referring now to FIG. 19, a treatment device 3001 is illustrated in accordance with another embodiment of the present invention. The device 3001 is similar to the devices 1, 1d-1i, 1001, 2001 except as described herein below. The description of the devices 1, 1d-1i, 1001, 2001 above generally applies to the device 3001 described below except with regard to the differences specifically noted below. A similar numbering scheme will be used for the device 3001 as with the devices 1, 1d-1i, 1001, 2001 except that a 3000-series number will be used.

The treatment device 3001 may comprise a plate structure 3200 and a penetrating element 3100. The penetrating element 3100 and the plate structure 3200 may be provided as separate components, whereby the penetrating element 3100 is coupled to the plate structure 3200. The penetrating element 3100 and the plate structure 3200 may be coupled together by any suitable means, such as but not limited to adhesive, fastener, and the like. Non-limiting examples of fasteners include miniature anchors, straps, buckles, tape, or any other restraints. Non-limiting examples of adhesives include cyanoacrylates, epoxy resins, thermosets, thermoplastics, elastomers, PDMS, epoxy, silicone-based, polyurethanes, or the like.

The penetrating element 3100 may comprise an outer surface and an inner surface. The penetrating element may be flexible and comprise an elongated body 3110 that extends along a longitudinal axis. The elongated body 3110 may comprise a first end 3120 (also referred to as "distal end") opposite a second end 3130 (also referred to as "proximal end"), whereby the longitudinal axis intersects both the first end 3120 and the second end 3130 of the elongated body 3110. The elongated body 3110 may extend a length $L_3$ as measured from the first end 3120 to the second end 3130, whereby the length $L_3$ ranges from about 5 mm to about 32 mm—including all lengths and sub-ranges therebetween.

The elongated body 3110 may comprise an outer surface and an inner surface, whereby the inner surface defines a passageway 3140 (also referred to herein as "lumen passageway") that extends through the elongated body 3110 along the longitudinal axis. The inner surface may be continuous and form a circular cross-section. The passageway 3140 may intersect the first end 3120 the elongated body 3110. The passageway 3140 may intersect the second end 3130 the elongated body 3110. The inner surface of the elongated body 3110 may form an open conduit that is the passageway 3140 that provides fluid communication between the first end 3120 and the second end 3130 of the elongated body 3110. The outer surface of the penetrating element 3100 may comprise the outer surface of the elongated body 3110.

In some embodiments a coating may be applied to the inner surface of the elongated body 3110 such that the inner surface of the penetrating element comprises the coating. In such embodiments, the coating may form the surfaces that define the lumen passageway 3140. In some embodiments a coating may be applied to the outer surface of the elongated body 3110 such that the outer surface of the penetrating element 3100 comprises the coating.

The outer surface of the elongated body 3110 may circumscribe the inner surface of the elongated body 3110, whereby both the inner surface and the outer surface are oriented about the longitudinal axis. The outer surface and the inner surface of the elongated body 3110 may be oriented concentrically about the longitudinal axis.

The elongated body 3110 may form a hollow cylindrical shape. The passageway 3140 may have an inner diameter as measured in a direction radially from the longitudinal axis to the inner surface of the penetrating element 3100. The inner diameter of the passageway 3140 may range from about 0.01 mm to about 5 mm—including all diameters and sub-ranges there-between. In a preferred embodiment, the inner diameter of the passageway 3140 may be less than about 1 mm. In a non-limiting example, the inner diameter of the passageway 3140 may be 0.01 mm, 0.05 mm, 0.11 mm, 0.15 mm, 0.2 mm, 0.25 mm, 0.3 mm, 0.35 mm, 0.4 mm, 0.45 mm, 0.5 mm, 0.55 mm, 0.6 mm, 0.65 mm, 0.7 mm, 0.75 mm, 0.8 mm, 0.85 mm, 0.9 mm, 0.95 mm, 1 mm, 2 mm, 3 mm, 4 mm, and 5 mm.

The elongated body 3110 may have an outer diameter as measured in a direction radially from the longitudinal axis. The outer diameter is the distance spanning opposite portions of the outer surface 3111 of the elongated body 3110. The outer diameter may be equal to about 101% to about 150% of the inner diameter—including all percentages and sub-ranges there-between. Stated otherwise, the inner diameter of the passageway 3140 is less than the outer diameter of the passageway 3140.

The penetrating element 3100—including the elongated body 3110—may be formed from a polymeric material. In some embodiments, the elongated body 3110 may be a polymer tube having a lumen. As embodied herein, the polymer may be a biocompatible polymer. The biocompatible polymer may be an organic polymer, an inorganic polymer, or blends thereof. Non-limiting examples of biocompatible polymer include silicone rubber, polyethylene, polypropylene, poly(methyl methacrylate) (PMMA), poly (tetrafluoroethylene) (PTFE), polystyrene, polyethylcyanoacrylate, poly(vinyl chloride) (PVC), polyether ether ketone (PEEK), polyether sulfone (PES), polymer gels and combinations thereof. In certain embodiments, the biocompatible polymer can include a single type of polymer or a combination of different polymers, e.g., as a polymer blend and/or copolymer. In certain embodiments, the polymeric matrix can be one or more flexible polymers and/or one or more solid polymers.

Although not shown, the penetrating element 3100 may further comprise at least one perforation on the elongated body 3110. Specifically, the perforation may extend outward radially from the longitudinal axis. The perforations may extend continuously from inner surface of the elongated body 3110 to the outer surface of the elongated body 3110. The perforations provide a passageway that creates fluid communication between the inner surface and the outer surface of the elongated body 3110. The perforations may extend continuously from inner surface of the penetrating element 3100 to the outer surface of the penetrating element 3100. The perforations provide a passageway that creates fluid communication between the inner surface of the penetrating element 3100 and the outer surface of the penetrating element 3100.

The perforations may be present on the penetrating element 3100 in a location that is adjacent to the first end 3120 of the elongated body 3110. The perforations may be present on the penetrating element 3100 in a location that is adjacent to the second end 3130 of the elongated body 3110. The perforations may increase the flow rate of fluid (e.g., aqueous humour) through the penetrating element 3100 via the passageway 3140.

According to some embodiments of the present invention, the treatment device 3001 may comprise the penetrating element 3100 coupled to the plate structure 3200. Specifically, at least a portion of the outer surface of the penetrating element 3100 may directly contact the first major exposed surface 3201 of the plate structure 3200. Direct contact may be maintained by thermal bonding or welding together the two surfaces.

In other embodiments, at least a portion of the outer surface of the penetrating element 3100 may indirectly contact the first major exposed surface 3201 of the plate structure 3200—whereby the indirect contact is the result of a coupling element being present between the outer surface of the penetrating element 3100 and the first major exposed surface 3201 of the plate structure 3200. Non-limiting examples of a coupling element may include adhesive or separate fastener, such as one or more anchors (e.g., a silicon anchor formed on the multi-directional plate), straps, buckles, elastic bands, tape, or any other suitable securing features. As described further herein, the penetrating element 3100 may also be coupled to the plate structure by geometric modifications aimed at securing the tubing to the plate.

When the penetrating element 3100 is coupled to the plate structure 3200, the penetrating element 3100 may overlay at least a portion of the first major exposed surface 3201 of the plate structure 3200 such that the portion of the first major exposed surface 3201 of the plate structure 3200 is no longer exposed (i.e., the portion is covered by the penetrating element 3100). In such configuration, at least one open-cell present on the first topography may be closed by the outer surface of the penetrating element 3100.

Although not shown, other embodiments include that the penetrating element 3100 may be coupled to the plate structure 3200 such that the penetrating element 3100 may overlay at least a portion of the second major exposed surface 3202 of the plate structure 3200 such that the portion of the second major exposed surface 3202 of the plate structure 3200 is no longer exposed (i.e., the portion is covered by the penetrating element 3100). In such configuration, at least one open-channel present on the second topography may be closed by the outer surface of the penetrating element 3100.

The penetrating element 3100 may be positioned relative to the plate structure 3200 such that the longitudinal axis of the elongated body 3110 is oriented substantially orthogonal to the cell axis A-A of the plate structure 3200. In other embodiments, the penetrating element 3100 may be positioned relative to the plate structure 3200 such that the longitudinal axis A-A of the elongated body 3110 is oriented oblique to the cell axis A-A of the plate structure 3200.

The side surface 3203 of the plate structure 3200 may form a perimeter of the first major exposed surface 3201 of the plate structure 3200—similarly, the side exposed surface 3203 forms a perimeter of the second major exposed surface 3202 of the plate structure 3200.

The following discussion is made in reference to the first major exposed surface 3201 but also applies to the second major exposed surface 3202. The first major exposed surface 3201 of the plate structure 3200 comprises a perimeter region $P_R$ that is adjacent to the perimeter formed by the side surface 3203. The first major exposed surface 3201 of the plate structure 3200 comprises a central region $C_R$ that is circumscribed by the perimeter region $P_R$.

The perimeter of the plate structure 3200 may form a symmetrical or asymmetrical boundary. In either embodiment, the plate structure 3200 may be generally centered about a central point 3208. The perimeter region $P_R$ and the central region $C_R$ may be concentric about the central point 208. In a non-limiting embodiment, the transition between the perimeter region $P_R$ and the central region $C_R$ may be delineated by the dotted boundary 3209 between the central region $C_R$ and the perimeter region $P_R$.

The boundary 3209 may be inset from the perimeter of the plate structure 3200 by a perimeter distance $D_P$—whereby the perimeter distance $D_P$ is a non-zero value. The boundary 3209 may conform to the geometry of the perimeter; however, the present invention does not limit the shape of the dotted boundary 3209 to any particular shape (e.g., polygon, circle, ellipsis, non-geometric shapes, etc.).

The first major exposed surface 3201 of the plate structure 3200 may have a first surface area. The perimeter distance $D_P$ may be equal to a value such that the perimeter region $P_R$ is equal to about 1% to about 50% of the first surface area. The perimeter distance $D_P$ may be equal to a value such that the central region $C_R$ may be equal about 50% to about 99% of the first surface area.

The treatment device 1 may comprise the penetrating element 3100 such that the second end 3130 of the elongated body 3110 lies within the perimeter region $P_R$ and the first end 3120 extends beyond the perimeter of the first major exposed surface 3201 of the plate structure 200. Stated otherwise, as shown in FIG. 19, the penetrating element 3100 may not overlay the central region $C_R$ of the plate structure 3200. In such embodiments, the amount of overlap between the penetrating element 3100 and the first major exposed surface 3201 of the plate structure 3200 may be equal to 1% to about 99% of the perimeter distance $D_P$—including all amounts and sub-ranges there-between.

According to this embodiment, the treatment device 3001 may be implanted onto the eye 900 such that the plate structure 3200 is located between the sclera 913 and conjunctiva 950 tissue. The penetrating element 3100 may extend from the plate structure 3200 through the sclera 913 and into the anterior chamber 990 of the eye 900 such that the first end 3120 of the penetrating element 3100 is located within the anterior chamber 990. Under this configuration, the penetrating element 3100 may function as a passageway to deliver excess fluid from anterior cavity to the plate structure 3200, which functions as an external reservoir for the excess fluid until it is absorbed by the surrounding tissue of the subject.

According to the embodiments where the plate structure 3200 comprises a multi-lobed geometry is trilobed, the plate structure 3200 may have a generally triangular shape—whereby the corners may be rounded. In such embodiment, the penetrating element 3100 may overlay the perimeter region PR (and optionally, the central region CR) such that the penetrating element 3100 does not intersect any of the lobes.

In such configuration, the elongated body 3110 of the penetrating element 3100 may intersect the perimeter 3203 of the plate structure 3200 and be located between the first and second lobe without intersecting the third lobe. In other embodiments, the elongated body 3110 of the penetrating element 3100 may intersect the perimeter 3203 of the plate structure 3200 and be located between the first and third lobe without intersecting the second lobe. In other embodiments, the elongated body 3110 of the penetrating element 3100 may intersect the perimeter 3203 of the plate structure 3200 and be located between the second and third lobe without intersecting the first lobe.

Figure 21:
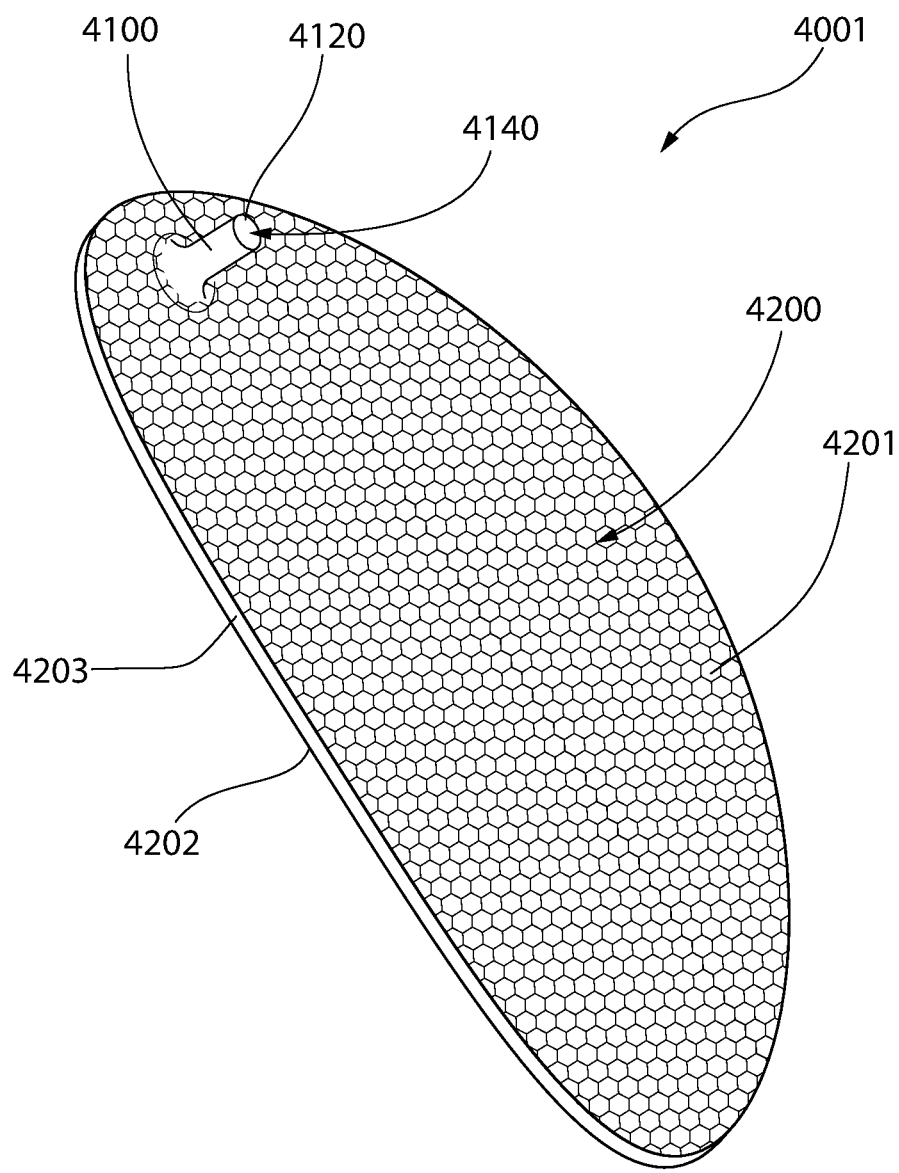
FIG. 21 is a perspective view of a treatment device according to another embodiment of the present invention.
Figure 22:
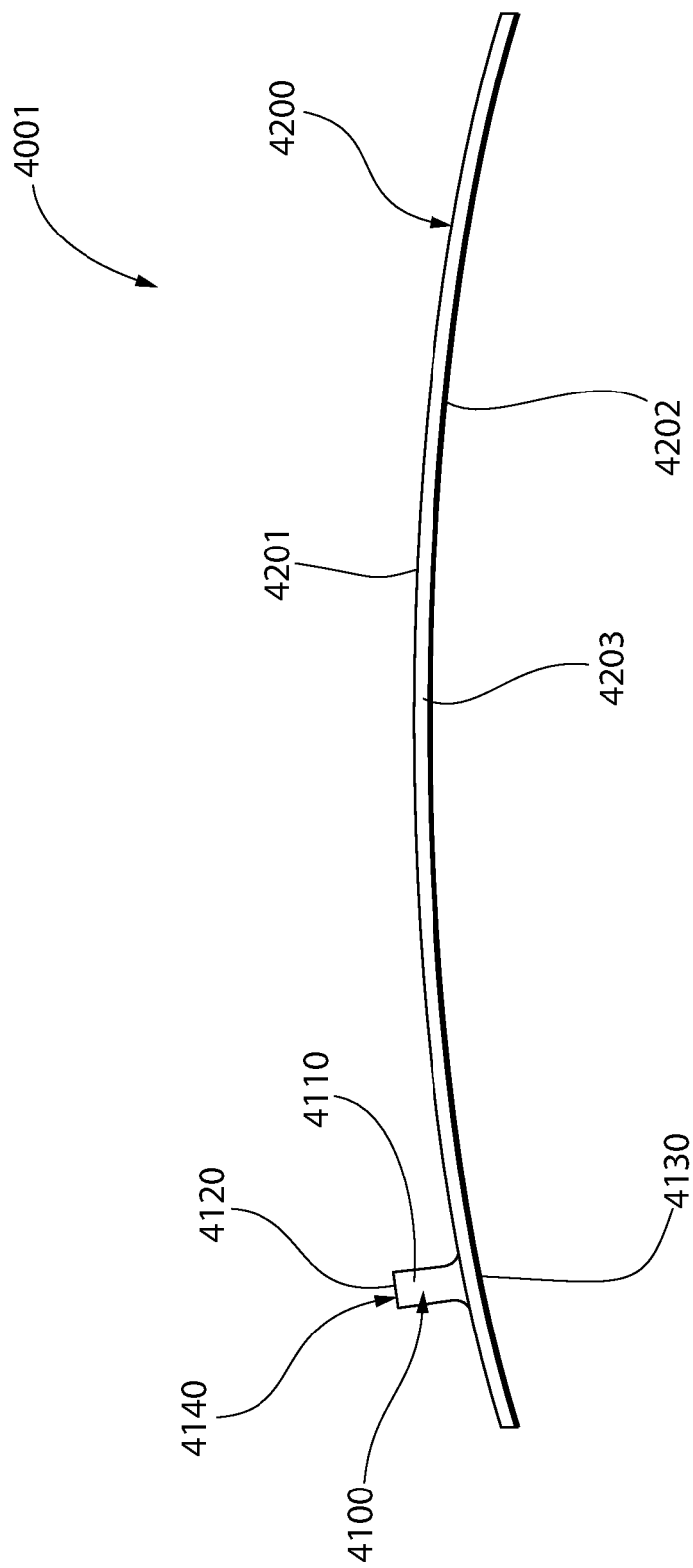
FIG. 22 is a side view of the treatment device of FIG. 21.

Referring now to FIGS. 21 and 22, a treatment device 4001 is illustrated in accordance with another embodiment of the present invention. The treatment device 4001 is similar to the treatment devices 1, 1d-1i, 2001, 3001, except as described herein below. The description of the treatment devices 1, 1d-1i, 2001, 3001, above generally applies to the treatment device 4001 described below except with regard to the differences specifically noted below. A similar numbering scheme will be used for the treatment device 4001 as with the treatment devices 1, 1d-1i, 2001, 3001, except that a 4000-series of numbering will be used.

According to this embodiment, the treatment device 4001 may comprise a penetrating element 4100 that forms a protuberance from at least one of the major surfaces 4201, 4202 of the plate structure 4200. The penetrating element 4200 according this embodiment may be coupled to or, alternatively, integrally formed with the plate structure 4200. In such embodiments, the protuberance component 4100 may be formed from a material that is the same material used to form the plate structure 4200. In other embodiments, the penetrating element 4200 may be the same general class of material used to form the plate structure 4200 (e.g., ceramic material) while each specific material may be different. In a non-limiting example, the plate structure 4200 and the penetrating element 4200 may both be formed from a ceramic material, wherein the multi-directional plate is formed from a first ceramic material (e.g., alumina) and the penetrating element 4200 is formed of a second ceramic material (e.g., silica), the first and second ceramic materials being different.

The penetrating element 4200 may extend along a longitudinal axis that is substantially orthogonal to the first and second major exposed surfaces 4201, 4202 of the plate structure 4200. The penetrating element 4200 may extend from a proximal end 4330 to a distal end 4320, whereby the proximal end 4330 is coupled to or integrally formed with the plate structure 4200.

The penetrating element 4300 may function as an integrally formed flow channel or pathway through or along the plate structure 4200. A flow channel 4340 may extend along the longitudinal axis such that it is oriented orthogonal to the first and second major exposed surfaces 4201, 4202 of the plate structure 4200. Alternatively, the outer surface of the penetrating element 4300 may create a pathway for intraocular fluid to flow along.

In other embodiments, the treatment device 1 of the present invention may be a material suitable for implantation into other regions of the eye 900 including but not limited to the cornea 910, the retina 941, the lens 930—as well as a stabilizing structure between various eye tissues, and a structure for directing fluid, chemicals, and/or signals between arts of the eye. Additions; spaces that may be suitable for implantation with the treatment device 1 of the present invention include uveoscleral outflow pathway, Schlemm's canal and collector channels, trabecular meshwork, and suprachoroidal space. In certain embodiments, more than one treatment device 1 can be implanted into one or multiple quadrants of the eye 900.

Examples

This Example illustrates the use of the drainage device to lower intraocular pressure and the tolerability of the device when implanted beneath the conjunctiva in New Zealand White Rabbits.

Materials and Methods

Fabrication of the drainage device: Honeycomb structures were designed and fabricated out of 53 nm-thick ALD alumina ($Al_2O_3$) and silica ($SiO_2$). The honeycomb structures were fabricated in different geometries with lateral dimensions varying between 0.5 and 10 millimeters. Three clamping configurations have been used: cantilevers, doubly clamped beams, and rectangular plates clamped on all four sides.

The fabrication started with a double side polished Si wafer. SiN films with a thickness of 180 nm were deposited on both sides using PECVD. Honeycomb structures with a height of 10 μm were patterned in silicon using photolithography and reactive ion etching (RIE). The back side was patterned via photolithography and the openings were obtained by RIE etching of SiN. The SiN mask was removed from the front side and the ALD layer was then deposited. For alumina deposition, trimethylaluminum (TMA) and water were used as precursors and two different temperatures, 150° C. and 250° C., were used. The deposition rates were measured using an ellipsometer to be 0.91 Å/cycle at 150° C. and 1.18 Å/cycle at 250° C.

In order to pattern the ALD layer, a thick layer of SPR 220 resist was spin-coated on the structure. The thickness of the resist was measured to be 14 μm. After the spin coating and soft baking at 105° C. the wafer was cooled down slowly to make sure the photoresist did not crack. After photolithography, inductively coupled plasma etching (ICP) with a BCl3-based chemistry process was used to pattern the alumina ALD layer. In contrast, RIE was used to pattern the silica ALD layer. Anisotropic KOH etching was next. Before placing the wafer in KOH, the top surface was covered with ProTek to prevent the ALD layer from being etched in the KOH solution. A silicon etching rate of 75 μm/hour was measured at 80° C. in the 30% KOH solution. By accurately timing the KOH etching process, it was possible to stop the process ~20 μm from the top surface. The exact depth was measured using a Zygo profilometer. After that, the ProTek layer was removed and oxygen plasma was performed to make sure the surface of the wafer was completely clean and without any polymer residue. In some embodiments, as an alternative to KOH etching, the silicon substrate can be partially removed using a laser micromachining system such as IPG Photonics IX-280-DSF. $XeF_2$ etching was used for the final release of the structure. Approximately 100 cycles (30 sec each) of $XeF_2$ etching with a ratio of 3.2:2 ($XeF_2:N_2$) was required for the complete release of the structures. A silicon tubing was coupled to the plate structure through a silicon anchor. The inner diameter of tubing was 0.5 mm. Prior to the surgery, a geometry of the plate structure was modified and the tubing was primed with balanced salt solution to obtain the desired length and shape.

Surgical Methods: Three experimentally naive New Zealand White rabbits (1 male and 2 females), approximately 5 months old and weighing 2.8 to 3.3 kilograms for males and females at the outset of the study were assigned to treatment groups as shown in the table 1 below.

TABLE 1

| GROUP | Left Eye | Right Eye | Number of Animals Male | Number of Animals Female |
|---|---|---|---|---|
| 1. Test Article | Insertion between the sclera and the conjunctiva via a conjunctival incision | Sham incision in the conjunctiva | 1 | 2 |

To implant the treatment device, each rabbit was anesthetized with a combination of Ketamine (40 mg/kg) and Xylazine (4 mg/kg) subcutaneously. Anesthetics were supplemented as needed. All drug usage was documented in the raw data. A few drops of 1% proparacaine (topical anesthesia) were placed in each eye at this time as well. Once anesthetized, the rabbit was placed in lateral recumbency and the area surrounding the eye prepped with a Swapstick containing 10% Providone-iodine. The eye was then rinsed with 0.9% sterile saline and another few drops of proparacaine given. A sterile drape was placed over the rabbit allowing exposure of the eye. Sterile instruments (steam autoclaved prior to first procedure and then chemically sterilized in chlorhexidine solution and rinsed with sterile water/saline between animals). Sterile gloves were worn.

The eyelid was kept open manually or with an eyelid speculum for the procedure. The eye was rotated medially using Colibri forceps and a small incision made in the conjunctiva lateral to the iris. A subconjunctival pocket was created ventrally and the treatment device placed within. Upon placement, the eye was allowed to rotate back to normal position and placement of the treatment device was observed to assure it is lying well within the subconjunctival pocket. The rabbit was then rotated to the other side and a sham procedure performed similarly on the contralateral eye, with no treatment device or other material implanted. Sterile ophthalmic ointment was placed on both eyes during the recovery period.

Observations and Measurements: The treatment device was implanted into the eye of the subjects on Day 1 via a conjunctival incision between the sclera and the conjunctiva. Mortality and clinical observations were evaluated daily. Ocular irritation scores were recorded prior to dose on Day 1, once daily on Days 2-5, Day 12, and Day 19. Body weights were recorded weekly. Food consumption was recorded daily. All animals were sacrificed on Day 21. The eyes with optic nerve for all animals were harvested at necropsy and evaluated microscopically.

Histological analysis: The animals were sacrificed with an overdose of an intravenous barbiturate on Day 21. All animals were necropsied. The eyes with optic nerve were collected and immediately fixed in Davidson's fixative for 24-48 hours. After the nerve specimens were dehydrated with increasing concentrations of ethanol (30-100%), the nerves were sectioned with a sharp razor blade. The sections were then embedded in paraffin in descending order and sectioned at 3 mm in thickness. The sections were stained with hematoxylin and eosin. Two sections (halves of the globe) with pupillary-optic disc orientation were trimmed from each eye, and two levels were microtomed per paraffin block, resulting in four slides per eye available for microphonic examination, Results and Discussion One male and two females New Zealand White rabbits were dosed once on Day 1 with the treatment device via a conjunctival incision between the sclera and the conjunctiva.

Mortality/Morbidity: There were no early deaths during the study. All animals survived until their scheduled sacrifice on Day 21.

Clinical Observations: On Day 1, mild to moderately decreased behavioral activity was noted post-surgery, and all animals had closed or partially closed eyes at 2-4 hours post-dose. These findings were considered test article unrelated and were secondary to the anesthesia and surgical procedures. All animals appeared normal on study days 2-21, and no clinical signs were noted.

Ocular Observations: The eyes of all animals (left and right) had ocular Draize scores of 0 prior to dosing on Day 1. Minimal overall Draize scores were recorded on study Days 2 and 3. Scores were noted in both, the left and right eye (drainage device implant and sham procedure, respectively). By Day 4, no ocular scores were noted. Table 2 below, summarizes the overall ocular Draize scores recorded during the study.

TABLE 2

| | Overall Ocular Draize Score | | | | | |
|---|---|---|---|---|---|---|
| | Left Eye Animal #s | | | Right Eye Animal #s | | |
| | 1414 | 1413 | 1416 | 1414 | 1413 | 1416 |
| Study Day 1 | 0 | 0 | 0 | 0 | 0 | 0 |
| Study Day 2 | 0 | 2 | 2 | 0 | 2 | 0 |
| Study Day 3 | 0 | 2 | 2 | 0 | 0 | 2 |
| Study Day 4 | 0 | 0 | 0 | 0 | 0 | 0 |
| Study Day 5 | 0 | 0 | 0 | 0 | 0 | 0 |
| Study Day 12 | 0 | 0 | 0 | 0 | 0 | 0 |
| Study Day 19 | 0 | 0 | 0 | 0 | 0 | 0 |

Body weight: No apparent test article-related effects on body weight or body weight gains were noted.

Food consumption: There were no test article-related effects on food consumption. The animals ate all their food on essentially all days.

Postmortem Observations

Gross necropsy findings: No gross necropsy findings were noted at scheduled sacrifice on Day 21.

Histopathology: The treatment device was not visible microscopically in any animal. A focal scleral [defect]←[or "alteration", since "defect" might imply a problem] was noted neat the limbus in several eyes, consisting of an elevation and separation of conjunctiva and superficial collagen fibers from the deeper collagen fibers of the sclera, creating an empty space. Aside from fragmentation of collagen, no notable tissue reaction was evident. While a defect of minimal (Grade 1) severity was noted in two control (right) eyes, defects of mild (Grade 2) to moderate (Grade 3) severity were evident in two out of three treated (left) eyes, rising suspicion that the tissue defects in the eyes receiving the treatment device could at least in part represent implant sites in which the implant fragmented or washed our during processing. Conjunctival hyperplasia, lymphoplasmacytic infiltrate, and/or fibrosis of minimal severity were noted near the limbus in right and left eyes of all three animals. These lesions can be explained as spontaneous background findings and/or associated with surgical manipulation.

In summary, no test related clinical observations, effects on body weight or body weight gains, or effects on food consumption were noted. Post-surgery, overall Draize scores were minimal and all eyes appeared normal by Day 4. No gross necropsy findings were noted at scheduled sacrifice on Day 21. The treatment device was not visible after tissue processing, and no tissue reaction was noted at the implant site. In conclusion, the treatment device when implanted beneath the conjunctiva in New Zealand White rabbits was well tolerated.

It will be understood that the foregoing only demonstrates the tolerability of a treatment device when implanted into the eye and is only illustrative of the principles of the present disclosure, and that various modifications can be made by those skilled in the art without departing from the scope and spirit of the present disclosure.

What is claimed is:

1. A method of reducing intraocular pressure comprising:
 a) securing a treatment device to an eye, the treatment device comprising a continuous plate structure that enables aqueous humor to flow from a first end to a second end, the first end having a maximum width that is narrower than a maximum width of the second end, the treatment device comprising:
  an uppermost surface opposite a lowermost surface, the uppermost surface including a plurality of open cells; and
  a fluid pathway including a plurality of open channels formed into the lowermost surface, the plurality of open channels configured in an intersecting grid pattern extending from the first end to the second end,
 wherein the treatment device enables aqueous humor to flow along the fluid pathway, thereby reducing intraocular pressure within the eye, and
 wherein the first end of the treatment device is inserted into an anterior chamber of the eye and the second end of the treatment device is inserted into at least one of an uveoscleral outflow pathway, Schlemm's canal, a collector channel, a supraciliary space, a trabecular meshwork, a subconjunctival space, or a suprachoroidal space of the eye.

2. The method according to claim 1, wherein the treatment device is secured onto a sclera of the eye.

3. The method according to claim 2, wherein after step a) the treatment device is located at an implant position in the eye such that a first major exposed surface of the plate structure faces a conjunctiva of the eye and a second major exposed surface of the plate structure faces the sclera of the eye.

4. The method according to claim 1, wherein the intersecting grid pattern includes a hexagonal grid pattern.

5. The method according to claim 1, wherein after step a), at least a portion of the treatment device is located between two adjacent eye muscles, wherein at least a portion of the treatment device is located between the lateral rectus muscle and the superior rectus muscle.

6. The method according to claim 1, wherein the first end of the treatment device is inserted into an anterior chamber of the eye and the second end of the treatment device is inserted between two adjacent eye muscles.

7. A method of reducing intraocular pressure comprising:
 causing a second end of a treatment device to be secured within drainage tissue of an eye of a patient; and
 causing a first end of the treatment device to be secured within an anterior chamber of the eye for receiving excess aqueous humor, the first end of the treatment device having a maximum width that is narrower than a maximum width of the second end of the treatment device, wherein the treatment device, including the first end and the second end, includes a continuous plate structure having an uppermost surface opposite a lowermost surface and a plurality of open channels formed into one of the uppermost surface or the lowermost surface, the plurality of open channels configured in an intersecting grid pattern extending from the first end to the second end of the treatment device, the continuous plate structure further comprising a plurality of open cells formed into the other of the uppermost surface and lowermost surface, wherein the plurality of open channels are configured in an intersecting grid pattern that defines a fluid pathway, wherein the treatment device enables aqueous humor to flow along the fluid pathway, thereby reducing intraocular pressure within the eye, and wherein the drainage tissue includes at least one of an uveoscleral outflow pathway, Schlemm's canal, a collector channel, a supraciliary space, a trabecular meshwork, a subconjunctival space, or a suprachoroidal space of the eye.

8. The method according to claim 7, wherein the second end of the treatment device is inserted between two adjacent eye muscles.

* * * * *